US006852318B1

(12) United States Patent
Varner

(10) Patent No.: US 6,852,318 B1
(45) Date of Patent: Feb. 8, 2005

(54) METHODS FOR DETECTING AND INHIBITING ANGIOGENESIS

(75) Inventor: Judith A. Varner, Encinitas, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/307,223

(22) Filed: May 7, 1999

Related U.S. Application Data
(60) Provisional application No. 60/084,850, filed on May 8, 1998.

(51) Int. Cl.$^7$ ...................... A61K 39/395; A61K 39/42
(52) U.S. Cl. ................................ 424/130.1; 424/133.1; 424/134.1; 424/138.1; 424/141.1; 424/143.1; 424/152.1; 424/178.1; 424/179.1
(58) Field of Search ........................... 514/2; 424/130.1, 424/131.1, 133.1, 134.1, 138.1, 141.1, 143.1, 152.1, 178.1, 179.1

(56) References Cited

U.S. PATENT DOCUMENTS

| | | | |
|---|---|---|---|
| 5,536,814 | A | 7/1996 | Ruoslahti et al. |
| 5,567,417 | A | 10/1996 | Sasisekharan et al. |
| 5,627,263 | A | 5/1997 | Ruoslahti et al. |
| 5,753,230 | A | 5/1998 | Brooks et al. |
| 5,766,591 | A | 6/1998 | Brooks et al. |
| 5,855,866 | A | 1/1999 | Thorpe et al. |
| 5,866,540 | A | 2/1999 | Jonczyk et al. |
| 5,922,676 | A | * 7/1999 | Pasqualini et al. |
| 6,177,542 | B1 | 1/2001 | Ruoslahti et al. |

FOREIGN PATENT DOCUMENTS

| | | |
|---|---|---|
| EP | 0906919 A2 | 4/1999 |
| WO | WO 93/15203 | 8/1993 |
| WO | WO 95/14714 | 1/1995 |
| WO | WO95/14714 | * 6/1995 |
| WO | WO 96/04304 | 2/1996 |
| WO | WO97/10507 | 3/1997 |
| WO | WO 97/33887 A1 | 9/1997 |
| WO | WO98/10795 | 3/1998 |
| WO | WO99/13329 | 3/1999 |

OTHER PUBLICATIONS

Gallin et al (Inflammation:Basic Principles and Clinical Correlates, Raven Press, New York, p. 552), 1988.*
Thorpe (Monoclonal Antibodies in Biological and Clinical Applications, Pinchera et al., eds., pp. 475–506), 1988.*
Guo et al (Cancer Research, 1997, 57:1737–1742).*
Scott et al (J. Invest. Derm., 1997, 108:147–153).*
Varner, J.A. et al., "Tumor Angiogenesis and the Role of Vascular Cell Integrin αvβ3," *Important Advances in Oncology*, 1996, pp. 69–87, Lippincott–Raven Publishers, Philadelphia, PA.
Varner, J.A. et al., "Integrins and Cancer," *Current Opinion in Cell Biology*, Oct. 1996, pp. 724–730.
Varner, J.A. et al., "Antagonists of Vascular Cell Integrin α5β1 Inhibit Angiogenesis," [reprint] *Circulation*, Oct. 27, 1998, p. 4166.
Thorpe in *Monoclonal Antibodies in Biological and Clinical Applications*, Pinchera et al., eds, 1995, pp. 475–506
Gallin et al., in Inflammation: Basic Principles and Clinical Correlates, Raven Press, NY, 1988, p. 552.
Takada et al. (1988) "Extracellular Matrix Receptors, ECM-RII and ECMRI, for Collagen and Fibronectin correspond to VLA–2 and VLA–3 in the VLA Family of Heterodimers," J. Cell. Biochem. 37:385–393.
Takada et al. (1987) "Fibronectin receptor structures in the VLA family of heterodimers," Nature 326:607–609.
Eliccs et al. (1991) "Receptor Functions for the Integrin VLA–3: Fibronectin, Collagen, and Laminin Binding are Differentially Influenced by Arg–Gly–Asp Peptide and by Divalent Cations," J. Cell Biol. 112:169–181.
Masumoto & Hemler (1993) "Multiple activation states of VLA–4. Mechanistic differences between adhesion to CS1/fibronectin and to vascular cell adhesion molecule–1," J. Biol. Chem. 268:228–234.
Zhang et al. (1993) "The αvβ 1 Integrin Functions as a Fibronectin Receptor But Does Not Support Fibronectin Matrix Assembly and Cell Migration on Fibronectin." J. Cell Biol. 122:235–242.
Ruegg et al. (1992) "Role of integrin α4β7/α4βP in Lymphocyte Adherence to Fibronectin and VCAM–1 and in Homotypic Cell Clustering," J. Cell Biol. 117:179–189.

(List continued on next page.)

Primary Examiner—Susan Ungar
(74) Attorney, Agent, or Firm—Townsend and Townsend and Crew LLP

(57) ABSTRACT

The present invention provides methods for reducing or inhibiting angiogenesis in a tissue, by contacting α5β1 integrin in the tissue with an agent that interferes with specific binding of the α5β1 integrin to a ligand expressed in the tissue; and methods of identifying angiogenesis in a tissue, by contacting the tissue with an agent that specifically binds α5β1 integrin, and detecting specific binding of the agent to α5β1 integrin associated with a blood vessel in the tissue. Also provided are methods of diagnosing a pathological condition characterized by angiogenesis in a tissue in an individual. The invention further provides methods of reducing or inhibiting angiogenesis in a tissue in an individual, by administering to the individual an agent that interferes with the specific binding of α5β1 integrin to a ligand expressed in the tissue; and methods of reducing the severity of a pathological condition associated with angiogenesis in an individual, by administering to the individual an agent that interferes with specific binding of α5β1 integrin to a ligand in a tissue associated with the pathological condition. The invention also provides methods of identifying an agent that reduces or inhibits angiogenesis associated with α5β1 integrin expression in a tissue by contacting a tissue exhibiting angiogenesis associated with α5β1 integrin expression with an agent, and detecting a reduction or inhibition of angiogenesis in the tissue.

29 Claims, 1 Drawing Sheet

OTHER PUBLICATIONS

Orlando and Cheresh (1991) "Arginine–Glycine–Aspartic Acid Binding Leading to Molecular Stabilization Between Integrin $\alpha_v\beta_3$ and Its Ligand," J. Biol. Chem. 266:19543–19550.

Suehiro et al. (1997) "Fibrinogen is a Ligand for Integrin $\alpha_5\beta_1$ on Endothelial Cells," J. Biol. Chem. 272:5360–5366.

Suehiro et al. (2000) "Fibrinogen Binds to Integrin $\alpha_5\beta_1$ via the Carboxyl–Terminal RGD site of the A$\alpha$–chain," J. Biochem. 128:705–710.

Felding Haberman et al. (1997) "A Single Immunoglobulin–like Domain of the Human Neural Cell Adhesion Molecule L1 Supports Adhesion by Multiple Vascular and Platelet Integrins." J. Cell Biol. 139:1567–1581.

Silletti et al. (2000) "Plasmin Sensitive Dibasic Sequences in the Third Fibronectin–like Domain of L–cell Adhesion Molecule (CAM) Facilitate Homomultimerization and Concomitant Integrin Recruitment," J. Cell Biol. 149:1485–102.

Rehn et al. (2001) "Interaction of endostatin with integrins implicated in angiogenesis" Proc. Natl. Acad. Sci. 98:1024–1029.

Carlson et al. (2001) "Direct Cell Adhesion to the Angiopoietins Mediated by Integrins," J. Biol Chem. 276:26516–26525.

Marcinkiewicz et al.(1999) "Structural and Functional Characterization of EMF10, a Heterodimeric Disintegrin from *Eristocophis macmahoni* Venom that Selectively Inhibits $\alpha_5\beta_1$ Integrin" Biochem. 38:13302–13309.

Wierzbicka–Potynowski et al. (1999) "Structural requirements of Echistatin for the Recognition of $\alpha_v\beta_3$ and $\alpha_5\beta_1$ Integrins," J. Biol. Chem. 274:37809–14.

Yi and Ruoslahti (2001) "A fibronectin fragment inhibits tumor growth, angiogenesis, and metastasis," Pro. Natl. Acad. Sci. 98:620–624.

Varner et al. (1995) "Integrin $\alpha_5\beta_1$ Expression Negatively Regulates Cell Growth: Reversal by Attachment to Fibronectin," Mol. Biol. Cell 6:725–740.

Morla et al. (1994) "Superfibronectin is a functionally distinct form of fibronectin," Nature 367:193–198.

Kim et al. (2000) "Regulation of Angiogenesis in Vivo by Ligation of Integrin $\alpha_5\beta_1$ with the Central Cell–Binding Domain of Fibronectin," Am. J. Pathol. 156:1345–1362.

Pasqualini et al. (1996) "A polymeric form of fibronectin has antimetastatic effects against multiple tumor types," Nature Med. 2:1197–1203.

Kumar et al. (1997) "Biochemical Characterization of the Binding of Echistatin to Integrin $\alpha_v\beta_3$ Receptor," J. Pharmacol. Experimen. Therap. 283:843–853.

Nowlin et al. (1993) "A Novel Cyclic Pentapeptide Inhibits $\alpha 4\beta 1$ and $\alpha 5\beta 1$ Integrin–mediated Cell Adhesion," J. Biol. Chem. 268:20352–20359.

Takagi et al. (1997) "Structural Interlock between Ligand-Binding Site and Stalk–Like Region of $\beta 1$ Integrin Revealed by a Monoclonal Antibody Recognizing Conformation–Dependent Epitope," J. Biochem. 121:914–921.

Kim et al. (2002) "Inhibition of endothelial cell survival and angiogenesis by protein kinase A," J. Clin. Invest. 110:933–941.

Clark et al. (1982) "Blood vessel fibronectin increases in conjunction ith endothelial cell proliferation and capillary ingrowth during wound healing," J Invest Dermatol. Nov;79(5):269–76.

Castellani et al. (1994) "The fibronectin isoform containing the ED–B oncofetal domain: a marker of angiogenesis," Int J Cancer. 59:612–618.

Neri et al. (1997) "Targeting by a affinity–matured recombinant antibody fragments of an angiogenesis associated fibronectin isoform," Nat Biotechnol. Nov; 15(12):1271–5.

Mariani et al. (1997) Tumor targeting potential of the monoclonal antibody BC–1 against oncofetal fibronectin in nude mice bearing human tumor implants, Cancer. Dec. 15;80(12 Suppl):2378–84.

Pasqualini et al. (1996) "A polymeric form of fibronectin has antimetastatic effects against multiple tumor types," Nature Medicine 2(1):1197–1203.; p. 1197, col. 2, last paragraph.

Kumar et al. (1997) "Biochemical characterization of the binding of echistatin to integrin v 3 receptor," Journal of Pharmacology and Experimental Therapeuctics, 283(2):843–853.

Aota, S., Nomizu, M., and Yamada, K.M. 1994, The short amino acid sequence Pro–His–Ser–Arg–Asn in human fibronactin enhances cell–adhesive function. J. Biol. Chem. 269: 24755–24761.

Arap W et al. 1997. Cancer treatment by targeted drug delivery to tumor vasculature in a mouse model. Science 279: 377–380.

Bader, B.L. et al. 1998. Extensive vasculogenesis, angiogenesis, and organogenesis precede lethality in mice lacking all $\alpha$v integrins. Cell 95: 507–519.

Bloch, W. et al. 1997. $\beta 1$ Integrin is essential for teratoma growth and angiogenesis. J. Cell Biol. 139: 265–278.

Blystone, S.D. et al. 1994. Integrin $\alpha$v$\beta 3$ differentially regulates adhesive and phagocytic functions of the fibronectin receptor $\alpha 5\beta 1$. J. Cell Biol. 127: 1129–1137.

Brooks, P.C. et al. 1994a. Requirement of vascular integrin alpha v beta 3 for angiogenesis. Science 264: 569–571.

Brooks, P.C. et al. 1994b. Integrin alpha v beta 3 antagonists promote tumor regression by inducing apoptosis of angiogenic blood vessels. Cell 79:1157–1164.

Brooks, P.C., et al. 1995. Anti–integrin alpha v beta 3 blocks human breast cancer growth and angiogenesis in human skin. J. Clin. Invest. 96: 1815–1822.

Carron, C.P. et al. 1998. A peptidomimetic antagonist of the integrin $\alpha$v$\beta 3$ inhibits Leydig cell tumor growth and development of hypercalcemia of malignancy. Cancer Res. 58: 1930–1955.

Charo, IF et al. 1990. The vitronectin receptor alpha v beta 3 binds fibronectin and acts in concert with alpha 5 beta 1 in promoting cellular attachment and spreading on fibronectin. J. Cell Biol. 111: 2795–800.

Christofidou–Solomidou, M. et al. 1997. Expression and function of endothelial cell $\alpha$v integrin receptors in wound-induced human angiogenesis in human skin/SCID mice chimeras. Am. J. Path. 151: 975–983.

Clark, R.A.F. et al. 1996. Transient functional expression of $\alpha$v$\beta 3$ on vascular cells during wound repair. Am. J. Path. 148: 1407–1421.

Collo, G. and Pepper, M.S. 1999. Endothelial cell integrin $\alpha 5\beta 1$ expression is modulated by cytokines and during migration in vitro. J. Cell Sci. 112: 569–578.

Drake, C.J. et al. 1992. Antibodies to beta 1–integrins cause alterations of aortic vasculogenesis, in vivo. Dev. Dyn. 193: 83–91.

Drake, C.J. et al. 1995. An antagonist of integrin $\alpha$v$\beta 3$ prevents maturation of blood vessels during embryonic neovascularization. J. Cell Science 108: 2655–2661.

Friedlander, M. et al. 1995. Definition of two angiogenic pathways by distinct alpha v integrins. Scienc 270:1500–1502.

Friedlander M. et al. 1996. Involvement of integrin αvβ3 and αvβ5 in ocular neovascular diseases. Proc. Natl. Acad. Sci. 93: 9764–9769.

George, E. L., et al. 1993. Defects in mesodermal migration and vascular development in fibronectin–deficient mice. Development 119: 1079–1091.

Goh, K. L. et al. 1997. Mesodermal defects and cranial neural crest apoptosis in α5 integrin–null embryos. Development 124: 4309–4319.

Lan, N. et al. 1998. Distinct signal transduction pathways are utilized during the tube formation and survival phase of in vitro angiogenesis. J. Cell Sci. 111: 3621–3631.

Kaczmarek, J. et al. 1994. Distribution of oncofetal fibronectin isoforms in normal hyperplastic and neoplastic human breast tissues. Int. J. Cancer 58: 11–16.

Koivunen, E. et al. 1993. Selection of peptides binding to the α5β1 integrin from a phage display library. J. Biol. Chem. 268: 20205–20210.

Koivunen, E., Wang, B., Ruoslahti, E. 1994. Isolation of a highly specific ligand for the α5β1 integrin from a phage display library. J. Cell Biol. 124: 373–380.

Magnusson, M.K. and Mosher D.F. 1998. Fibronectin: Structure, assembly, and cardiovascular implications. Arterioscler. Thromb. Vasc. Biol. 18: 1363–1370.

Neri, D. Carnemolla, B., Nissim, A. Blaza, E., Leprini, A., Querze, G., Pina, A., Tarli, L., Halin, C., Neri, P., Zardi, L. Winter, G. 1997. Targeting by affinity–matured recombinant antibody fragments of an angiogenesis associated fibronectin isoform, Nature Biotech. 15: 1271–1275.

Pierschbacher, M.D., Hayman, EG; and Ruoslahti, E. 1981. Location of the cell–attachment site in fibronectin with monoclonal antibodies and proteolytic fragments of the molecule. Cell 26: 259–67.

Pytela, R. et al. 1985. Identification and isolation of a 140 κD cell surface glycoprotein with properties expected of a fibronectin receptor. Cell 40: 191–98.

Ruoslahti, E. et al. 1981. Alignment of biologically active domains in the fibronectin molecule. J. Biol. Chem. 256:7277–81.

Sechler, J. L. and Schwartzbauer, J.E. 1998 Control of cell cycle progression by fibronectin matrix architecture. J. Biol. Chem. 273: 25533–25536.

Senger, D.R. et al. 1996. Stimulation of endothelial cell migration by vascular permeability factor/vascular endothelial growth factor through cooperative mechanisms involving the alphav beta3 integrin, osteopontin, and thrombin. Am. J. Pathol. 149: 1–7.

Senger, D. R. et al. 1997. Angiogenesis promoted by vascular endothelial growth factors: Regulation through α1β1 and α2β1 integrins. Proc. Nat'l Acad. Sci. USA 94: 13612–13617.

Simon, K.O. et al. 1997. The αvβ3 integrin regulates α5β1–mediated cell migration toward fibronectin. J. Biol. Chem. 272: 29380–29389.

Stromblad S., et al. 1996. Suppression of p53 activity and p21WAF1/CIP1 expression by vascular cell integrin alphaV-beta3 during angiogenesis. J Clin Invest 98: 426–433.

Stromblad, S., and Cheresh, D. A. 1996. Integrins, angiogenesis and vascular cell survival. Chemistry and Biology 3: 881–885.

Varner, J.A. 1997. The role of vascular cell integrin αvβ3 and αvβ5 in angiogenesis., *Regulation of Antgiogenesis* (ed. by I.D. Goldberg & E.M. Rosen Birkhauser Verlag, Basl/Switzerland) Exs. 79: 361–390.

Varner, J.A. et al. 1995. Integrin α5β1 expression negatively regulates cell growth: reversal by attachment to fibronectin. Mol. Biol. Cell 6: 725–740.

Yang, J.T., et al. 1993. Embryonic mesodermal defects in α5 integrin–deficient mice. Development 119: 1093–1105.

Kim, Semi, et al., "Regulation of Angiogenesis in Vivo by Ligation of Integrin α5β1 with the Central Cell–Binding Domain of Fibronectin", *American Journal of Pathology*, (2000), 156(4): 1345–1362.

Ruoslahti, Erkki, "Integrin Signaling and Matrix Assembly", *Tumor Biology*, (1996) 17(2):117–124.

Yano, Yoshiko, et al, "Cyclic Strain Induces Reorganization of Integrin $α_5β_1$ and $α_2β_1$ in Human Vein Endothelial Cells", *Journal of Cellular Biochemistry*, (1997) 64(3):505–513.

Zhang, Zhuohua, et al. "The α5β1 integrin supports survival of cells on fibronectin and up–regulates Bc1–2 expression", *Proc. Natl. Acad. Sci USA*, (1995) 92:6161–6165.

* cited by examiner

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 1
```

```
-continued

Cys Arg Arg Glu Thr Ala Trp Ala Cys
  1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence:   SYNTHETIC
      PEPTIDE

<400> SEQUENCE: 2

Cys Ala Thr Ala Glu Arg Trp Arg Cys
  1               5
```

METHODS FOR DETECTING AND INHIBITING ANGIOGENESIS

This application claims the benefit of priority of U.S. Provisional Application Ser. No. 60/084,850 to Judith A. Varner, filed May 8, 1998, now abandoned, and entitled A NOVEL METHOD FOR THE DETECTION AND INHIBITION OF ANGIOGENESIS, the entire contents of which is incorporated herein by reference.

This invention was made, in part, with government support under grant number R01 CA71619 awarded by the National Cancer Institute. The government has certain rights in the invention.

BACKGROUND OF THE INVENTION

1. Field of the Invention

This invention relates generally to methods for detecting and treating conditions involving undesirable angiogenesis and more specifically to methods of detecting or inhibiting angiogenesis by interfering with specific binding of $\alpha 5\beta 1$ integrin to a ligand.

2. Background Information

Angiogenesis is the process whereby new blood vessels are formed. Angiogenesis, also called neovascularization, occurs normally during embryogenesis and development, and occurs in fully developed organisms during wound healing and placental development. In addition, angiogenesis occurs in various pathological conditions, including in ocular diseases such as diabetic retinopathy and macular degeneration due to neovascularization, in conditions associated with tissue inflammation such as rheumatoid arthritis and inflammatory bowel disease, and in cancer, where blood vessel formation in the growing tumor provides oxygen and nutrients to the tumor cells, as well as providing a route via which tumor cells metastasize throughout the body. Since millions of people around the world are afflicted by these diseases, a considerable effort has been made to understand the mechanisms involved in angiogenesis in the hope that such an understanding will allow the development of methods for detecting and inhibiting such undesirable angiogenesis.

Angiogenesis occurs in response to stimulation by one or more known growth factors, and also may involve other as yet unidentified factors. Endothelial cells, which are the cells that line mature blood vessels, normally do not proliferate. However, in response to an appropriate stimulus, the endothelial cells become activated and begin to proliferate and migrate into unvascularized tissue, to form new blood vessels. In some cases, precursor cells can be activated to differentiate into endothelial cells, which form new blood vessels.

Blood vessels are surrounded by an extracellular matrix. In addition to stimulation by growth factors, angiogenesis depends on interaction of the endothelial cells with the extracellular matrix, as well as with each other. The activation of endothelial cells by growth factors and the migration into and interaction with the extracellular matrix and with each other is dependent on cell surface receptors expressed by the endothelial cells. These cell surface receptors, which include growth factor receptors and integrins, interact specifically with particular molecules.

In pathological conditions such as age-related macular degeneration and diabetic retinopathy, decreasing availability of oxygen to the retina results in a hypoxic condition that stimulates the secretion of angiogenic growth factors such as vascular endothelial growth factors (VEGF), which induce abnormal migration and proliferation of endothelial cells into tissues of the eye. Such vascularization in ocular tissues can induce corneal scarring, retinal detachment and fluid accumulation in the choroid, each of which can adversely affect vision and lead to blindness.

Angiogenesis also is associated with the progression and exacerbation of inflammatory diseases, including psoriasis, rheumatoid arthritis, osteoarthritis, and inflammatory bowel diseases such as ulcerative colitis and Crohn's disease. In inflammatory arthritic disease, for example, influx of lymphocytes into the region surrounding the joints stimulates angiogenesis in the synovial lining. The increased vasculature provides a means for greater influx of leukocytes, which facilitate the destruction of cartilage and bone in the joint. Angiogenic vascularization that occurs in inflammatory bowel disease results in similar effects in the bowel.

The growth of capillaries into atherosclerotic plaques in the coronary arteries represents another pathological condition associated with growth factor induced angiogenesis. Excessive blood flow into neovascularized plaques can result in rupture and hemorrhage of the blood-filled plaques, releasing blood clots that can result in coronary thrombosis.

The involvement of angiogenesis in such diverse diseases as cancer, ocular disease and inflammatory diseases has led to an effort to identify methods for specifically inhibiting angiogenesis as a means to treat these diseases. For cancer patients, such methods of treatment can provide a substantial advantage over currently used methods such as chemotherapy, which kill or impair not only the target tumor cells, but also normal cells in the patient, particularly proliferating normal cells such as blood cells, epithelial cells, and cells lining the intestinal lumen. Such non-specific killing by chemotherapeutic agents results in side effects that are, at best, unpleasant, and can often result in unacceptable patient morbidity, or mortality. In fact, the undesirable side effects associated with cancer therapies often limit the treatment a patient can receive.

For other pathological conditions associated with abnormal angiogenesis such as diabetic retinopathy, there are no effective treatments short of retinal transplants. However, even if retinal transplantation is performed, the new retina would be subject to the same conditions that resulted in the original retinopathy. Thus, there exists a need to identify the molecular interactions involved in the undesirable angiogenesis that occurs in certain pathological conditions such that methods for diagnosing and specifically treating such pathologies can be developed. The present invention satisfies this need and provides related advantages as well.

SUMMARY OF THE INVENTION

The present invention provides methods for reducing or inhibiting angiogenesis in a tissue, by contacting $\alpha 5\beta 1$ integrin associated with blood vessels in the tissue with an agent that interferes with specific binding of the $\alpha 5\beta 1$ integrin to a ligand expressed in the tissue, thereby reducing or inhibiting angiogenesis in the tissue. In one embodiment, the agent is an $\alpha 5\beta 1$ antagonist that does not substantially interfere with the specific binding of an integrin other than $\alpha 5\beta 1$ integrin to its ligand, for example, $\alpha V\beta 3$ integrin binding to vitronectin. In another embodiment, the $\alpha 5\beta 1$ integrin ligand is fibronectin.

A method of the invention is useful, for example, for reducing or inhibiting angiogenesis in ocular tissue such as retina, macula or cornea; in skin; in synovial tissue; in intestinal tissue; or in bone. In addition, a method of the invention is useful for reducing or inhibiting angiogenesis in a neoplasm, which can be benign or malignant and, where malignant, can be a metastatic neoplasm. As such, the invention provides medicaments, which contain α5β1 antagonists and are useful for reducing or inhibiting angiogenesis in an individual. An agent useful in practicing a method of the invention can be a peptide, for example, a peptide containing the amino acid sequence CRRETAWAC (SEQ ID NO: 1); an antibody, for example, an anti-α5β1 integrin antibody or an α5β1 integrin binding fragment thereof; or a nonpeptide, small organic molecule, for example, (S)-2-{(2,4,6-trimethyl phenyl)sulfonyl}amino-3-{7-benzyloxycarbonyl-8-(2-pyridinylaminomethyl)-1-oxy-2,7-diazaspiro-{4,4}-non-2-en-3-yl}carbonylamino} propionic acid. An agent useful as an α5β1 antagonist can be linked to a cytotoxin, for example, a cancer chemotherapeutic drug.

The invention also provides methods of identifying the presence of angiogenesis in a tissue by contacting the tissue with an agent that specifically binds α5β1 integrin, and detecting specific binding of the agent to α5β1 integrin associated with a blood vessel in the tissue. The agent can be a peptide, an antibody, or a nonpeptide, small organic molecule, and can be linked to a detectable label, which can be detected directly, or the presence of which can be detected due to its interaction with a particular reagent. Such a method is useful for identifying the presence of angiogenesis in various tissues, including in normal tissues such as embryonic tissue or placental tissue, in granulation tissue, or in a tissue involved in a pathological condition such as a neoplasm, a retinopathy, or an arthritic condition or other inflammatory condition.

The invention further provides methods of diagnosing a pathological condition characterized by angiogenesis in a tissue in an individual. A method of diagnosis can be performed, for example, by obtaining a sample of the tissue from the individual, wherein, in an individual having the pathological condition, the tissue exhibits angiogenesis; contacting the sample with an agent that specifically binds α5β1 integrin; and detecting specific binding of the agent to α5β1 integrin associated with a blood vessel in the tissue, thereby diagnosing a pathological condition characterized by angiogenesis in the individual. The pathological condition can involve the eye, for example, diabetic retinopathy or macular degeneration; the skin, for example, a hemangioma or psoriasis; a joint, for example, rheumatoid arthritis or osteoarthritis; or the intestine, for example Crohn's disease or ulcerative colitis; or can be a neoplasm, which can be benign or malignant. A malignant neoplasm, which can be metastatic, can be, for example, a breast carcinoma, colon carcinoma, ovarian carcinoma, or pancreatic carcinoma.

A method of diagnosing a pathological condition characterized by angiogenesis in a tissue in an individual also can be performed by administering an agent that specifically binds α5β1 integrin to an individual suspected of having the pathological condition; and detecting specific binding of the agent to α5β1 integrin associated with a blood vessel in the tissue. The agent can be detectably labeled, for example, by linking it to a moiety such as a radionuclide, a paramagnetic material or an X-ray attenuating material. The method of detecting can be an in vivo imaging method such as a radionuclide imaging, positron emission tomography, computerized axial tomography, or magnetic resonance imaging method, or can be an ex vivo method, wherein, following administration of the agent, a sample of the tissue is obtained from the individual, and specific binding of the agent in the sample is detected. Agent that is specifically bound to α5β1 integrin in such a sample can be detected directly, for example, by detecting radioactivity due to the moiety linked to the agent, or can be detected indirectly by contacting the specifically bound agent with a reagent that specifically interacts with the agent, or with the moiety, and detecting an interaction of the reagent with the agent or the moiety.

The present invention further provides methods of reducing or inhibiting angiogenesis in a tissue in an individual, by administering to the individual an agent that interferes with the specific binding of α5β1 integrin to a ligand expressed in the tissue, thereby reducing or inhibiting angiogenesis in the tissue in the individual. Also provided is a method of reducing the severity of a pathological condition associated with angiogenesis in an individual, by administering to the individual an agent that interferes with specific binding of α5β1 integrin to a ligand in a tissue associated with the pathological condition, thereby reducing or inhibiting angiogenesis in the tissue and, consequently, reducing the severity of the pathological condition. The condition can be any pathological condition associated with angiogenesis, including a neoplasm, which can be a malignant neoplasm, for example, a carcinoma such as breast carcinoma, colon carcinoma, ovarian carcinoma or pancreatic carcinoma, or a sarcoma, mesothelioma, teratocarcinoma, an astrocytoma, glioblastoma, or other neoplasm, including a metastatic malignant neoplasm. The agent can be administered by various routes, for example, intravenously, orally, or directly into the region to be treated, for example, directly into a neoplastic tumor; via eye drops, where the pathological condition involves the eye; or intrasynovially, where the condition involves a joint.

The invention also provides methods of identifying an agent that reduces or inhibits angiogenesis associated with α5β1 integrin expression in a tissue. Such a method, which is useful as a screening assay, can be performed by contacting a tissue exhibiting angiogenesis associated with α5β1 integrin expression with an agent, and detecting a reduction or inhibition of angiogenesis in the tissue. Contacting of the tissue with the agent can occur in vivo or ex vivo. Where the method is performed using an in vitro format, it readily can be adapted for automated, high throughput screening assays. The tissue can be any tissue that undergoes angiogenesis associated with α5β1 integrin expression, for example, malignant neoplastic tissue, and can be from any individual, including, for example, from a mammal, bird, reptile or amphibian.

DETAILED DESCRIPTION OF THE INVENTION

Figure 1:
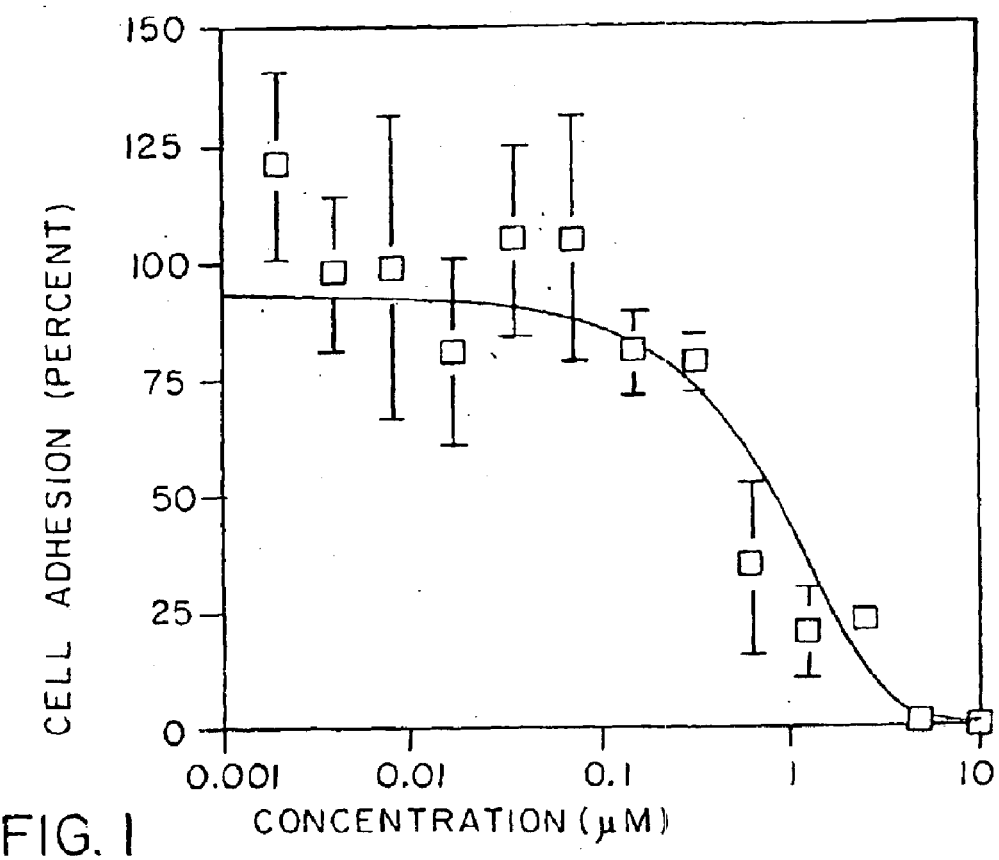
FIG. 1 demonstrates the inhibitory effect of the nonpeptide small organic molecule, SJ749, on α5$^+$ HT29 tumor cell adhesion to fibronectin. α5$^+$ HT29 tumor cells were produced by transfecting HT29 cells with α5$^+$ cDNA.

The present invention provides methods for detecting angiogenesis in a tissue by identifying α5β1 binding to a ligand in a blood vessel in the tissue. Methods of diagnosing the presence of angiogenesis in an individual also are provided. The invention further provides methods for reducing or inhibiting angiogenesis in a tissue by interfering with the specific binding of α5β1 integrin to a ligand expressed in the tissue. Methods of reducing or inhibiting angiogenesis, which can be associated with a pathological condition, in an individual, also are provided.

Angiogenesis depends on the cooperation of various growth factors and cell adhesion events. The αV integrins have been shown to play critical roles in angiogenesis, although studies using αV integrin null mice have suggested that other adhesion receptors and their ligands also may be involved in angiogenesis. As disclosed herein, the integrin α5β1 and its ligand fibronectin are coordinately upregulated during growth factor stimulated angiogenesis and on blood vessels present in human tumor biopsies, and the interaction of these molecules is required for the angiogenesis that occurs during and supports tumor growth in vivo, as well as angiogenesis associated with various pathological conditions.

The development of vascular networks during embryogenesis or normal and pathological angiogenesis depends on stimulation induced by growth factors (Breier and Risau, Trends in Cell Biology 6:454–456 (1996); Breier et al., Thromb. Haemost. 78:678–683 (1997); Folkman, Nature Med. 1:27–31 (1995); Risau, Nature 386:671–674 (1997)) and on cellular interactions with the extracellular matrix (Stromblad and Cheresh, Chemistry and Biology 3:881–885 (1996); Varner, Exs. 79:361–390 (1997); each of the publications cited in this disclosure is incorporated herein by reference). Genetic and functional analyses indicate that extracellular components and cell surface receptors regulate endothelial cell growth, survival and differentiation in vasculogenesis and in angiogenesis (George et al., Development 119:1079–1091 (1993); Yang et al.,Development 119:1093–1105 (1993); Stromblad and Cheresh, supra, 1996; Bloch et al.,J. Cell Biol. 139: 265–278 (1997); Varner, supra, 1997; Risau, supra, 1997; Bader et al., Cell 95:507–519 (1998)).

Blood vessels arise during embryogenesis by two processes, vasculogenesis and angiogenesis (Risau, supra, 1997), and the role of growth factors in both processes is well established. For example, vascular endothelial growth factor (VEGF; Ferrara et al., Nature 380:439–442 (1996)) and its receptors (de Vries et al., Science 255:989–991 (1992); Fong et al., Nature 376:66–70 (1995); Millauer et al., Cell 72:835–846 (1993); Shalaby et al., Cell 89:981–990 (1997)), and basic fibroblast growth factor (bFGF; Basilico and Moscatelli, Adv. Cancer Res. 59:115–165 (1992)) promote the initial development of the embryonic vascular network, and are involved in the formation of new blood vessels from pre-existing vessels during development, wound healing and the female reproductive cycle. VEGF (Warren et al., J. Clin. Invest. 95:1789–1797 (1995); Yoshida et al.,Mol. Cell. Biol. 17:14015–4023 (1997); Kong et al., Human Gene Ther. 9:823–833 (1998)), bFGF (Stan et al., J. Neurosurg. 82:1044–1052 (1995); Chopra et al., J. Canc. Res. Clin. Oncol. 123:167–172 (1997); Czubayko et al., Nature Med. 3:1137–1140 (1997); Yoshida et. al., supra, 1997), Interleukin-8 (IL-8; Arenberg et al., J. Clin. Invest. 97: 2792–2802 (1996); Luca et al., Am. J. Path. 151:1105–1113 (1997); Keane et al.,. J. Immunol. 159:1437–43(1997);Yatsunami et al., Cancer Lett. 120:101–108 (1997); Yoshida et al.,Invest. Ophthamol. Vis. Sci. 39:1097–1106 (1998)), and tumor necrosis factor-α (TNFα; Yoshida et. al., supra, 1997) are some of the growth factors that have a role in the angiogenesis that is associated with various pathological conditions, including, for example, solid tumor growth, diabetic retinopathy, and rheumatoid arthritis.

While growth factors stimulate new blood vessel growth, adhesion to the extracellular matrix (ECM) regulates endothelial cell survival, proliferation and motility during new blood vessel growth (Stromblad and Cheresh, supra, 1996; Varner, supra, 1997). Specific integrins or their ligands also influence vascular development and angiogenesis. For example, the αV integrins participate in angiogenesis by providing survival signals to activated endothelial cells (Arap et al., Science 279:377–380 (1997); Brooks et al., Science 264: 569–571 (1994a); Carron et al., Cancer Res. 58:1930–1955 (1998); Clark et al., Amer. J. Pathol. 148:1407–1421 (1997); Drake et al., Devel. Dyn. 193:83–91 (1992); Clark et al., J. Cell Science 108:2655–2661 (1995); Friedlander et al., Science 270:1500–1502 (1995)). However, some aspects of angiogenesis also can proceed in the absence of αV integrins (Bader et. al., supra, 1998), suggesting that other molecules, including the β1 integrin family, may compensate for the absence αV integrins during development (Drake et al., supra, 1992; Bloch et al., supra, 1997; Senger et al., Proc. Natl. Acad. Sci., USA 94:13612–13617 (1997)).

While active roles for integrins in the promotion of angiogenesis have been identified, the cognate ECM ligands for integrins that are involved in angiogenesis in vivo are less well described. One ECM protein, fibronectin, is expressed in provisional vascular matrices and provides proliferative signals to vascular cells during wound healing, atherosclerosis, and hypertension (Magnusson and Mosher, Arterioscler Thromb. Vasc. Biol. 18:1363–1370 (1998)). Fibronectin expression is upregulated on blood vessels in granulation tissues during wound healing (Clark et al., J. Invest. Dermatol. 79:269–276 (1982)), and an isoform of fibronectin, the ED-B splice variant, is preferentially expressed on blood vessels in fetal and tumor tissues, but not on normal quiescent adult blood vessels (Castellani et al., Int. J. Cancer 59:612–618 (1994); Kaczmarek et al., Int. J. Cancer 58:11–16 (1994); Neri et al., Nature Biotech. 15:1271–1275 (1997)). These observations suggest that fibronectin may have a role in angiogenesis. In addition, animals that lack fibronectin die early in development from a collection of defects, including missing notochord and somites as well as an improperly formed vasculature (George et al., supra, 1993). Prior to the present disclosure, however, a direct functional role for fibronectin in vasculogenesis or in angiogenesis was not established.

Several integrins bind to fibronectin (Hynes, Cell 69:11–25 (1992)), and integrin α5β1 generally is selective for fibronectin (Pytela et al., Cell 40:191–98 (1985)). Studies have demonstrated that loss of the gene encoding the integrin α5 subunit is embryonic lethal in mice and is associated with a complete absence of the posterior somites and with some vascular and cardiac defects (Yang et al., supra, 1993; Goh et al., Development 124: 4309–4319 (1997)). It was unclear, however, whether integrin α5β1 has a direct role in the regulation of vascular development or of angiogenesis in particular.

As disclosed herein, both fibronectin and its receptor, α5β1 integrin, directly regulate angiogenesis. Moreover, the specific interaction of fibronectin and α5β1 is central to the contribution of these two molecules to angiogenesis. Integrin α5β1 participates in pathways of angiogenesis that are the same as those of integrin αVβ3, but distinct from the pathways involving αVβ5. It is further disclosed herein that agents that interfere with the specific binding of α5β1 and fibronectin can reduce or inhibit growth factor stimulated angiogenesis and the angiogenesis that occurs in tumors and, therefore, can be useful for treating various pathological conditions, including malignant neoplasms.

The participation of the central cell binding domain of fibronectin and its receptor α5β1 in angiogenesis is disclosed herein. Expression of both integrin α5β1 and fibronectin were significantly enhanced on blood vessels of human tumors and in growth factor stimulated tissues, while these molecules were minimally expressed on normal human vessels and on unstimulated tissues (Example I). In addition, antibody antagonists, which bind the central cell binding domain of fibronectin and anti-α5β1 antibodies, as well as two other classes of α5β1 antagonists (peptides and nonpeptide, small organic molecule antagonists) blocked growth factor stimulated angiogenesis in chick chorioallantoic membrane (CAM; Example II) and in human skin grown on SCID mice (Example III). Antagonists of integrin α5β1 blocked bFGF, TNFα and IL-8 stimulated angiogenesis, but had a minimal. effect on VEGF-induced angiogenesis. Each of these α5β1 antagonists inhibited tumor angiogenesis and resulted in tumor regression in animal model systems (Example IV). Antagonists of fibronectin function also blocked both bFGF and VEGF angiogenesis, suggesting that other fibronectin receptors are involved in VEGF-mediated angiogenesis.

The results disclosed herein demonstrate that the expression of integrin α5β1 and fibronectin in angiogenesis is coordinated. When the expression of each molecule is minimal, as on unstimulated, quiescent blood vessels, antagonists of each molecule and addition of fibronectin to chick chorioallantoic membranes (CAM's) had little effect on angiogenesis. In contrast, after stimulation with growth factors, α5β1 and fibronectin expression are enhanced and blood vessels become sensitive to agents that act as antagonists of either molecule, as well as to the effects of exogenously added fibronectin. VEGF stimulation does not increase α5β1 expression, supporting the observation that VEGF angiogenesis is refractory to antagonists of α5β1. This result is substantiated by a report that in vitro expression of integrin α5β1 on endothelial cells was upregulated in response to bFGF (Collo and Pepper, *J. Cell Sci.* 112:569–578 (1999)), and that VEGF failed to upregulate α5β1 expression (Senger et al., *Am. J. Pathol.* 149:1–7 (1996); Senger et al., *Proc. Natl. Acad. Sci. USA* 94:13612–13617 (1997)). Thus, the functional roles of integrin α5β1 and fibronectin in angiogenesis likely are a direct consequence of their growth factor induced expression.

Antibodies directed against the central cell binding fragment of fibronectin, which contains the RGD integrin binding site, inhibited angiogenesis (Examples II and III). These antibodies likely interfere with the specific binding of α5β1 integrin to fibronectin, and, consequently, with possible downstream signal transduction events in vivo. Stimulation of bFGF angiogenesis by fibronectin and its cell binding domain in an α5β1-dependent manner indicate that α5β1 is the integrin receptor for fibronectin during angiogenesis. The absence of integrin α5β1 expression in VEGF stimulated angiogenesis likely accounts for the failure of fibronectin to enhance VEGF angiogenesis, even though antibodies directed against the cell binding peptide of fibronectin blocked VEGF angiogenesis. The results disclosed herein are the first demonstration of a direct in vivo role for fibronectin in angiogenesis.

The results disclosed herein also are the first to clearly identify a role for an extracellular matrix protein in the promotion of angiogenesis. Although collagens have been suggested to have roles in vascular development, intact collagens do not support endothelial cell outgrowth, survival or proliferation (Ilan et al., *J. Cell Sci.*111:3621–3631 (1998); Isik et al., *J. Cell. Phys.*175:149–155 (1999)). In fact, inhibition of the collagen receptors integrins α2β1 and α1β1 prevented the formation of large blood vessels and promoted the formation of small vessels (Senger et al., supra, 1997). Those results suggest that α2β1, α1β1, and their ligand, collagen, are involved in blood vessel maturation, rather than in the promotion of new blood vessel sprouts.

A functional role for integrin α5β1 in angiogenesis was established by demonstrating that agents that antagonize α5β1 binding to its ligand blocked angiogenesis induced by growth factors and angiogenesis in tumor fragments (Examples II, III and IV). Like α5β1, αVβ3 can serve as a fibronectin receptor (Charo et al.,*J. Cell Biol.* 111:2795–800 (1990)), although, as disclosed;. herein, endothelial cells use α5β1 as the major fibronectin receptor when both integrins are expressed.

The expression of α5β1 and αVβ3 is regulated by similar growth factors, and both integrins have a significant role in bFGF, TNFα, IL-8 and tumor-induced angiogenesis, but not in VEGF-induced angiogenesis (see Examples; see, also, Brooks et al., supra, 1994a; Brooks et al., *Cell* 79:1157–1164 (1994b); Friedlander et al., supra, 1995). These two integrins likely influence the same angiogenesis pathways, since combinations of their antagonists in angiogenesis animal models were neither additive nor synergistic (see Example II).

Binding of integrins to extracelluar matrix proteins promotes cell attachment, migration, invasion, survival and proliferation (Varner, supra, 1997), and antagonists of αVβ3 induce apoptosis of proliferating endothelial cells in vitro and in vivo (Brooks et al., supra, 1994b; Stromblad et al., supra, 1996). As disclosed herein, α5β1 antagonists also induce apoptosis of growth factor stimulated endothelial cells in vitro and in vivo.

Antagonists of α5β1 blocked tumor angiogenesis and growth (Example IV), similar to antagonists of integrin αVβ3 (Brooks et al., supra, 1994b, 1995). The tumor cell lines used for in vivo tumorigenicity and angiogenesis studies (Example IV) were integrin α5β1 negative, to discount any direct effect of the antagonists on the tumor cells, and remained α5β1 negative through the course of their culture on CAM's. HT29 tumors express a variety of growth factors, including VEGF, TNFα, TGFα, TGFβ, PDGF and IL-8; it is not known whether HT29 cells also express bFGF. VEGF is most commonly associated with the hypoxic core of the tumor, and is transcriptionally regulated by hypoxia, whereas bFGF and other factors are associated with the growing edge of the tumor (Shweiki, et. al., supra, 1992; Kumar et al., *Oncol. Res.* 10:301–311 (1998)). As observed for growth factor stimulated CAM's, α5β1 antagonists did not impact large pre-existing vessels on the CAM that underlie the transplanted tumors. These results demonstrate that agents that interfere with specific binding of α5β1 to its ligands, particularly fibronectin, can reduce or inhibit angiogenesis. The use of such agents, therefore, can provide a clinical benefit to individuals suffering from various pathological conditions, including to cancer patients.

As used herein, the term "integrin" refers to the extracellular receptors that are expressed in a wide variety of cells and bind to specific ligands in the extracellular matrix. The specific ligands bound by integrins can contain an arginine-glycine-aspartic acid tripeptide (Arg-Gly-Asp; RGD) or a leucine-aspartic acid-valine tripeptide, and include, for example, fibronectin, vitronectin, osteopontin, tenascin, and von Willebrand's factor. The integrins comprise a superfamily of heterodimers composed of an α subunit and a β subunit. Numerous α subunits, designated, for example, αV, α5 and the like, and numerous β subunits, designated, for example, β1, β2, β3, β5 and the like, have been identified, and various combinations of these subunits are represented in the integrin superfamily, including α5β1, αVβ3 and αVβ5. The superfamily of integrins can be subdivided into families, for example, as αV-containing integrins, including αVβ3 and αVβ5, or the β1-containing integrins, including α5β1 and αVβ1. Integrins are expressed in a wide range of organisms, including *C. elegans, Drosophila* sp., amphibians, reptiles, birds, and mammals, including humans.

As disclosed herein, antibody, peptide and nonpeptide small organic molecule antagonists of α5β1 can interfere with the specific binding of α5β1 integrin with its ligands, particularly fibronectin, in vascular tissue, and can reduce or inhibit angiogenesis (see Examples II, III and IV). Such molecules that interfere with the specific binding of α5β1 with its ligands are referred to herein generally as "agents," "agent antagonists" or "α5β1 antagonists." As used herein, the term "specific binding" or "binds specifically," when used in reference to the interaction of two or more molecules, means that the molecules can associate with each other under in vivo conditions and in vitro when incubated under appropriate conditions, which can mimic in vivo conditions. The terms "specifically interact" and "specific association" also are used to refer to molecules that specifically bind.

For purposes of the present invention, the molecules that specifically interact with each other generally are a receptor-type molecule and its ligand, including, for example, an integrin and its particular ligand or ligands, or an antibody and its particular antigen or antigens. It is recognized, however, that other molecules, for example, an α integrin subunit and a β integrin subunit also interact specifically to form an integrin heterodimer, as can an α5β1 antagonist and an α5β1 integrin. Methods for determining whether two molecules specifically interact are disclosed herein, and methods of determining binding affinity and specificity are well known in the art (see, for example, Harlow and Lane, *Antibodies: A laboratory manual* (Cold Spring Harbor Laboratory Press, 1988); Friefelder, "Physical Biochemistry: Applications to biochemistry and molecular biology" (W. H. Freeman and Co. 1976)).

Antibodies, peptides and nonpeptide small organic molecule antagonists that interfere with the specific binding of α5β1 with fibronectin are exemplified (see Example II). As used herein, the term "interfere," when used in reference to the action of an agent antagonist on the specific interaction of a receptor and its ligand, means that the affinity of the interaction is decreased below the level of binding that occurs in the absence of the agent. The skilled artisan will recognize that the association of a receptor and its ligand is a dynamic relationship that occurs among a population of such molecules such that, at any particular time, a certain proportion of receptors and ligands will be in association. An agent that interferes with the specific interaction of a receptor and its ligand, therefore, reduces the relative number of such interactions occurring at a given time and, in some cases, can completely inhibit all such associations.

The term "antagonist" is used herein to mean an agent, which can be an antibody, a peptide or a nonpeptide small organic molecule, that can interfere with the specific interaction of a receptor and its ligand. An anti-α5β1 integrin antibody, which can interfere with the binding of α5β1 with fibronectin, thereby reducing or inhibiting the association of α5β1 integrin with fibronectin, is an example of an α5β1 antagonist. An antagonist can act as a competitive inhibitor or a noncompetitive inhibitor of α5β1 binding to its ligand.

It can be difficult to distinguish whether an antagonist completely inhibits the association of a receptor with its ligand or reduces the association below the limit of detection of a particular assay. Thus, the term "interfere" is used broadly herein to encompasses reducing or inhibiting the specific binding of a receptor and its ligand. Furthermore, an agent can interfere with the specific binding of a receptor and its ligand by various mechanism, including, for example, by binding to the ligand binding site, thereby interfering with ligand binding; by binding to a site other than the ligand binding site of the receptor, but sterically interfering with ligand binding to the receptor; by binding the receptor and causing a conformational or other change in the receptor, which interferes with binding of the ligand; or by other mechanisms. Similarly, the agent can bind to or otherwise interact with the ligand to interfere with its specifically interacting with the receptor. For purposes of the methods disclosed herein for interfering with the specific interaction of an α5β1 integrin and its ligand, an understanding of the mechanism by which the interfering occurs is not required and no mechanism of action is proposed.

An agent that acts as an antagonist for α5β1 integrin binding to its ligand can be an antibody, particularly an anti-α5β1 antibody or an anti-fibronectin antibody. As used herein, the term "antibody" is used in its broadest sense to include polyclonal and monoclonal antibodies, as well as antigen binding fragments of such antibodies. With regard to an anti-integrin antibody, particularly an anti-α5β1 antibody, the term "antigen" means an integrin, particularly an α5β1 integrin protein, polypeptide, or peptide portion thereof, which may or may not include some or all of an RGD binding domain. An anti-α5β1 antibody, or antigen binding fragment thereof, is characterized by having specific binding activity for an α5β1 integrin of at least about $1 \times 10^5$ $M^{-1}$, generally at least about $1 \times 10^6$ $M^{-1}$, and particularly at least about $1 \times 10^7$ $M^{-1}$. Fab, F(ab')$_2$, Fd or Fv fragments of an anti-α5β1 antibody, which retain specific binding activity for the α5β1 integrin are included within the definition of an antibody.

The term "antibody" as used herein encompasses naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference. These and other methods of making, for example, chimeric, humanized, CDR-grafted, single chain, and bifunctional antibodies are well known to those skilled in the art (Winter and Harris, *Immunol. Today* 14:243–246 (1993); Ward et al., *Nature* 341:544–546 (1989); Harlow and Lane, supra, 1988; Hilyard et al., *Protein Engineering: A practical approach* (IRL Press 1992); Borrabeck, *Antibody Engineering*, 2d ed. (Oxford University Press 1995); each of which is incorporated herein by reference).

Anti-integrin antibodies, including anti-α5β1 antibodies, can be purchased from a commercial source, for example, Chemicon, Inc. (Temecula Calif.), or can be raised using as an immunogen a substantially purified full length integrin, which can be a human integrin, mouse integrin or other mammalian or nonmammalian integrin that is prepared from natural sources or produced recombinantly, or a peptide portion of an integrin, which can include a portion of the RGD binding domain, for example, a synthetic peptide. A non-immunogenic peptide portion of an integrin such as a human α5β1 can be made immunogenic by coupling the hapten to a carrier molecule such bovine serum albumin (BSA) or keyhole limpet hemocyanin (KLH), or by expressing the peptide portion as a fusion protein. Various other carrier molecules and methods for coupling a hapten to a carrier molecule are well known in the art and described, for example, by Harlow and Lane (supra, 1988).

Particularly useful antibodies for performing a method of the invention are those that specifically bind to an α5β1 integrin. Such antibodies are particularly useful where they bind α5β1 with at least an order of magnitude greater affinity than they bind another integrin, for example, αVβ3 or αVβ5. An anti-fibronectin antibody also can be useful in a method of the invention, particularly an anti-fibronectin antibody that interferes with binding of fibronectin to α5β1 integrin, but not to αVβ3 or other integrins.

As disclosed herein, an anti-α5β1 antibody was used to detect regions of growth factor stimulated angiogenesis, as occurs in a pathological condition (see Example I). The presence or amount of α5β1 integrin expression can be identified, for example, in a tissue sample, which can be a histological section obtained from a tissue or organ of an individual suspected of having a pathology characterized, at least in part, by undesirable angiogenesis. The identification of the presence or level of an α5β1 integrin expression in the sample can be made using well known immunoassay or immunohistochemical methods (Harlow and Lane, supra, 1988). An anti-α5β1 antibody, particularly an antibody that prevents ligand binding to the α5β1 integrin, also can be used in a screening assay to identify agents that compete for ligand binding to the integrin. As disclosed herein, such agents can be useful for inhibiting α5β1 mediated angiogenesis.

Peptides that specifically bind to α5β1 also are useful as antagonists of α5β1 binding to its ligands, including fibronectin. As discussed for anti-α5β1 antibodies, a peptide that specifically binds α5β1 can be useful in a method of the invention where the antibody binds to α5β1 with at least about a two-fold greater specificity than it binds to another integrin, for example, αVβ3, is more useful if it has at least about a five-fold greater specificity for α5β1, and is particularly useful if it has at least about a one order of magnitude greater specificity for α5β1 than for an integrin such as αVβ3. As such, the various RGD and RLD containing peptides that have been identified based on their relatively high binding affinity for αVβ3 or for αVβ5 (PCT/US94/13542) are not considered peptide antagonists of α5β1 binding to its ligand, as defined herein.

The term "peptide" is used broadly herein to include oligomers and polymers of amino acids or amino acid analogs that are linked by a peptide bond or an analog of a peptide bond. As such, the term "peptide" includes molecules commonly referred to as peptides, which generally contain about two to about fifty amino acids, as polypeptides, which generally contain about twenty to fifty amino acids or more, and as proteins, which can include peptides or polypeptides that, for example, are post-translationally modified. Thus, peptide antagonists contain two or more amino acids, which can be L-amino acids or D-amino acids, chemically modified amino acids, which can be naturally occurring or non-naturally occurring amino acids, or amino acid analogs. Peptides useful as α5β1 antagonists that reduce or inhibit angiogenesis can be identified by screening libraries of peptides, which can be prepared using well known methods of chemical synthesis (see, for example, Koivunen et al., supra 1993, 1994), or can be purchased from commercial sources.

Figure 2:
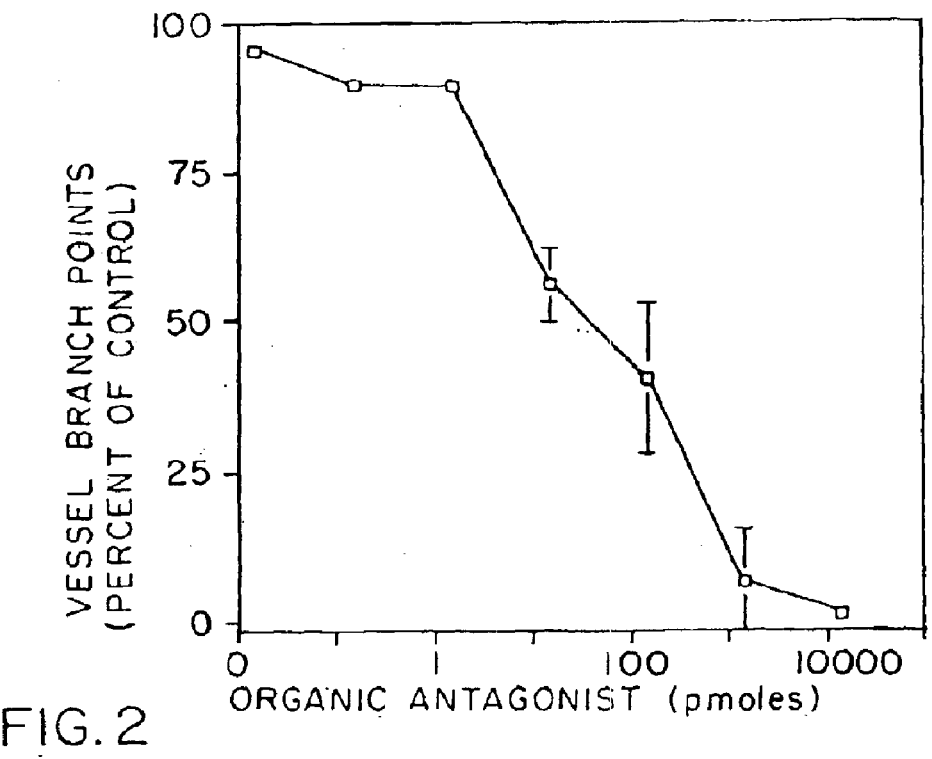
FIG. 2 demonstrates the dose dependent inhibitory effect of SJ749 on blood vessel branch point formation in chorioallantoic membranes (CAM's). Angiogenesis was stimulated by treatment of the CAM's with basic fibroblast growth factor.

An agent that interferes with α5β1 binding to its ligand also can-be a nonpeptide, small organic molecule, including a peptidomimetic, which is an organic molecules that mimics the structure of a peptide; or a peptoid such as a vinylogous peptoid. A nonpeptide small organic molecule that acts as an antagonist to the specific interaction of α5β1 integrin binding to a ligand, fibronectin, can be, for example, a heterocycle having the general structure (S)-2-phenylsulfonylamino-3-{{{8-(2-pyridinyl aminomethyl)-}-1-oxa-2-azaspiro-{4,5}-dec-2-en-yl}carbonylamino}propionic acid, as exemplified herein by the molecule designated SJ749, which has the structure: (S)-2-{(2,4,6-trimethylphenyl) sulfonyl}amino-3-{7-benzyloxycarbonyl-8-(2-pyridinyl aminomethyl)-1-oxa-2,7-diazaspiro-{4,4}-non-2-en-3-yl}carbonylamino}propionic acid (see Examples II and IV; U.S. Pat. No. 5,760,029). As disclosed herein, SJ749 interfered with α5β1 binding to fibronectin and reduced or inhibited angiogenesis in a dose dependent manner (see FIG. 2). Additional nonpeptide, small organic molecule α5β1 antagonists useful in a method of the invention can be identified by screening, for example, chemically modified derivatives of a heterocycle having the structure disclosed above, including chemically modified derivatives of SJ749, or other libraries of nonpeptide, small organic molecules (see below).

The present invention provides methods for reducing or inhibiting angiogenesis in a tissue, by contacting α5β1 integrin in the tissue with an agent that interferes with specific binding of the α5β1 integrin to a ligand expressed in the tissue, thereby reducing or inhibiting angiogenesis in the tissue. A particularly useful agent antagonist interferes with the binding of α5β1 to fibronectin, but does not substantially interfere with the specific binding of the ligand to an integrin other than α5β1 integrin. As disclosed herein, an agent such as an anti-α5β1 antibody, a peptide, or a nonpeptide small organic molecule that interferes with binding of α5β1 integrin to its ligand can reduce or inhibit growth factor stimulated angiogenesis and angiogenesis that occurs during tumor growth (see Examples II, III and IV).

As used herein, the phrase "reduce or inhibit," when used in reference to angiogenesis, means that the amount of new blood vessel formation that occurs in the presence of an agent antagonist is decreased below the amount of blood vessel formation that occurs in the u absence of an exogenously added agent antagonist. The terms "reduce" and "inhibit" are used together because it is recognized that the amount of angiogenesis can be decreased below a level detectable by a particular assay method and, therefore, it may not be possible to determine whether angiogenesis is reduced to a very low level or completely inhibited. Nevertheless, it will be clear from the particular assay being used that, in response to an agent that interferes with α5β1 integrin to its ligand, angiogenesis in a tissue is decreased below the level of angiogenesis in corresponding untreated tissue. Methods for determining an amount of blood vessel formation in a tissue, including the immunohistochemical methods disclosed herein (Example I), are well known in the art.

A method of the invention is useful, for example, for reducing or inhibiting angiogenesis in ocular tissue such as retina, macula or cornea; in skin such as occurs with psoriasis; in synovial tissue; in bone; or in intestinal tissue, by interfering with α5β1 binding to a ligand such as fibronectin in the tissue. In addition, a method of the invention is useful for reducing or inhibiting angiogenesis in a neoplasm, which can be benign or malignant and, where malignant, can be a metastatic neoplasm. An agent useful in practicing a method of the invention can be a peptide, for example, a peptide containing the amino acid sequence CRRETAWAC (SEQ ID NO: 1); an antibody, for example, an anti-α5β1 integrin antibody or an α5β1 integrin binding fragment thereof; or a nonpeptide, small organic molecule, for example, (S)-2-{(2,4,6-trimethylphenyl) sulfonyl}amino-3-{7-benzyloxycarbonyl-8-(2-pyridinylaminomethyl)-1-oxy-2,7-diazaspiro-{4,4}-non-2-en-3-yl}carbonylamino}propionic acid (SJ749). If desired, the agent can be linked to a cytotoxin such as ricin or a cancer chemotherapeutic drug, provided linkage of the cytotoxin does not substantially reduce the ability of the agent to specifically bind α5β1 integrin and interfere with the binding of α5β1 to its ligand.

The invention also provides methods of identifying the presence of angiogenesis in a tissue, by contacting the tissue with an agent that specifically binds α5β1 integrin, and detecting specific binding of the agent to α5β1 integrin associated with a blood vessel in the tissue, thereby identifying the presence of angiogenesis in the tissue. The agent can be a peptide, an antibody, or a nonpeptide, small organic molecule, and can be linked to a detectable label, which can be detected directly, or the presence of which can be detected due to its interaction with a particular reagent. Such a method is useful for identifying the presence of angiogenesis in various tissues, including, for example, normal tissues such as embryonic tissue or placental tissue, granulation tissue, and a tissue involved in a pathological condition. As such, the invention further provides methods of diagnosing a pathological condition characterized by angiogenesis associated with α5β1 integrin expression in a tissue in an individual.

The term "pathological condition" is used broadly herein to mean any abnormal physical or physiological condition characterized, at least in part, by angiogenesis associated with α5β1 integrin expression on newly forming blood vessels in a tissue. Such pathological conditions are exemplified by neoplasms (see Example I), ocular diseases such as diabetic retinopathy and macular degeneration associated with neovascularization, skin diseases such as psoriasis and hemangiomas, gingivitis, arthritic conditions such as rheumatoid arthritis and osteoarthritis, and inflammatory bowel diseases. Other pathological conditions amenable to a diagnostic or other method of the invention can be identified using methods such as those disclosed in Example I or otherwise known in the art.

The term "neoplasm" is used broadly herein to mean any new, pathological tissue growth. For purposes of the present invention, a neoplasm generally results in the formation of a tumor, which is characterized, in part, by angiogenesis. A neoplasm can be benign, for example, a hemangioma, glioma, teratoma, and the like, or can be malignant, for example, a carcinoma, sarcoma, glioblastoma, astrocytoma, neuroblastoma, retinoblastoma, and the like. The term "tumor" is used generally to refer to a benign or malignant neoplasm, and the term "cancer" is used generally to refer to a malignant neoplasm, which may or may not be metastatic. Malignant neoplasms that can be diagnosed using a method of the invention include, for example, carcinomas such as lung cancer, breast cancer, prostate cancer, cervical cancer, pancreatic cancer, colon cancer and ovarian cancer; and sarcomas such as osteosarcoma and Kaposi's sarcoma, provided the neoplasm is characterized, at least in part, by angiogenesis associated with α5β1 expression by the newly forming blood vessels (see Examples I and III).

A method of diagnosis can be performed, for example, by obtaining a sample of the tissue from the individual, wherein, in an individual having the pathological condition, the tissue exhibits angiogenesis; contacting the sample with an agent that specifically binds α5β1 integrin; and detecting specific binding of the agent to α5β1 integrin associated with a blood vessel in the tissue. An individual to be diagnosed or treated using a method of the invention can be any individual exhibiting angiogenesis associated with α5β1 integrin expression and, therefore, can be, for example, a vertebrate such as a mammal, including a human, dog, cat, horse, cow, or goat; a bird; or any other animal, particularly a commercially important animal or a domesticated animal.

A method of diagnosing a pathological condition characterized by angiogenesis in a tissue in an individual also can be performed by administering an agent that specifically binds α5β1 integrin to an individual suspected of having the pathological condition; and detecting specific binding of the agent to α5β1 integrin associated with a blood vessel in the tissue. The agent can be detectably labeled, for example, by linking the agent to a moiety, which is selected based, for example, on whether specific binding of the agent is to be detected in vivo or whether a tissue to which the agent is suspected of binding is to be removed, for example, by biopsy, and examined ex vivo.

A moiety useful for labeling an agent antagonist can be a radionuclide, a paramagnetic material, an X-ray attenuating material, a fluorescent, chemiluminescent or luminescent molecule, a molecule such as biotin, or a molecule that can be visualized upon reaction with a particular reagent, for example, a substrate for an enzyme or an epitope for an antibody. The moiety can be linked to an agent using well known methods, which are selected, in part, based on the chemical nature of the agent and the moiety. For example, where the moiety is an amino acid sequence such as a hexahistidine (His6) sequence, and the agent is a peptide, the His6 sequence can be synthesized as part of the peptide, and the His6-labeled agent can be identified by the binding of a nickel ion reagent to the His6 moiety. Methods for chemically linking a moiety to an agent also can be utilized (see, for example, Hermanson, *Bioconjugate Techniques*, (Academic Press 1996), which is incorporated herein by reference).

A specifically bound agent can be detected in an individual using an in vivo imaging method such as a radionuclide imaging, positron emission tomography, computerized axial tomography, or magnetic resonance imaging method, or can be detected using an ex vivo method, wherein, following administration, a sample of the tissue is obtained from the individual, and specific binding of the agent in the sample is detected. An agent that is specifically bound to α5β1 integrin in a sample can be detected directly, for example, by detecting the agent or by detecting the presence of a moiety such as by detecting radioactivity emitted by a radionuclide moiety. Specifically bound agent also can be detected indirectly by further contacting it with a reagent that specifically interacts with the agent, or with a moiety linked to the agent, and detecting interaction of the reagent with the agent or label. For example, the moiety can be detected by contacting it with an antibody that specifically binds the moiety, particularly when the moiety is linked to the agent. The moiety also can be, for example, a substrate, which is contacted by an enzyme that interacts with and changes the moiety such that its presence can be detected. Such indirect detection systems, which include the use of enzymes such as alkaline phosphatase, horseradish peroxidase, beta-galactosidase and the like, are well known in the art and commercially available, as are the methods for incorporating or linking the particular moiety to a particular type of agent.

The present invention further provides methods of reducing or inhibiting angiogenesis in a tissue in an individual, by administering to the individual an agent that interferes with the specific binding of α5β1 integrin to a ligand expressed in the tissue, thereby reducing or inhibiting angiogenesis in the tissue in the individual. As such, the invention provides methods of reducing the severity of a pathological condition associated with angiogenesis in an individual, by administering to the individual an agent that interferes with specific binding of α5β1 integrin to a ligand in a tissue associated with the pathological condition, thereby reducing or inhibiting angiogenesis in the tissue, and, consequently, reducing the severity of the pathological condition.

As used herein, the term "reducing the severity of a pathological condition" means that adverse clinical signs or symptoms associated with the pathological condition are ameliorated. A reduction in the severity of a pathologic condition can be detected by various methods, including routine clinical tests such as blood tests, which can used to determine relevant enzyme levels or circulating antigen or antibody; imaging tests, which can be used to detect a decrease in the growth rate or size of a neoplasm; or an ophthalmic procedure, which can be used to identify a reduction in the number of blood vessels in the retina of a diabetic patient. Such clinical tests are selected based on the particular pathological condition being treated. A reduction in the severity of a pathological condition also can be detected based on comments made by the patient being treated, for example, that a patient suffering from arthritis feels less pain or has greater joint mobility, or that a patient with diabetic retinopathy or with macular degeneration due to neovascularization can see more clearly, or the like.

Where an agent that interferes with the specific binding of an α5β1 integrin to its ligand is to be administered to a living individual, for example, for a diagnostic or therapeutic procedure, the agent generally will be in the form of a pharmaceutical compositions comprising the agent or agents and a pharmaceutically acceptable carrier. Pharmaceutically acceptable carriers are well known in the art and include aqueous solutions such as physiologically buffered saline or other buffers or solvents or vehicles such as glycols, glycerol, oils such as olive oil or injectable organic esters. The selection of a pharmaceutically acceptable carrier will depend, in part, on the chemical nature of the agent, for example, whether the agent is an antibody, a peptide or a nonpeptide, small organic molecule.

A pharmaceutically acceptable carrier can physiologically acceptable compounds that act, for example, to stabilize the agent or increase its absorption, or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the agent and on the particular physio-chemical characteristics of the agent.

Angiogenesis associated with α5β1 integrin expression can occur locally, for example, in the retina of an individual suffering from diabetic retinopathy, or can occur more systemically, for example, in an individual suffering from rheumatoid arthritis or a metastatic malignant neoplasm. Since regions of such angiogenesis can be localized or can more systemically dispersed, one skilled in the art would select a particular route and method of administration of an agent that interferes with the specific binding of an α5β1 integrin with its ligand, for example, fibronectin, based, in part, on this factor. For example, in an individual suffering from diabetic retinopathy, where angiogenesis associated with α5β1 integrin expression is localized to the retina, the agent can be formulated in a pharmaceutical composition convenient for use as eye drops, which can be administered directly to the eye. In comparison, in an individual suffering from a metastatic carcinoma, the agent in a pharmaceutical composition that can be administered intravenously, orally or by another method that distributes the agent systemically. Thus, an agent antagonist can be administered by various routes, for example, intravenously, orally, or directly into the region to be treated, for example, directly into a neoplastic tumor; via eye drops, where the pathological condition involves the eye; or intrasynovially, where the condition involves a joint.

The amount of an α5β1 agent antagonist that is administered to an individual will depend, in part, on whether the agent is administered for a diagnostic purpose or for a therapeutic purpose. Methods for determining an effective amount of an agent to administer for a diagnostic or a therapeutic procedure are well known in the art and include phase I, phase II and phase III clinical trials. An agent is administered in an effective amount, which is an amount sufficient to interfere with the specific binding of α5β1 integrin to its specific ligand in an individual. Generally, an agent antagonist is administered in a dose of about 0.0001 to 100 mg/kg body weight.

As disclosed herein, systemic administration of 5 μg anti-α5β1 antibody/2 ml blood volume of chick embryo inhibited 50% of the growth factor stimulated angiogenesis (Example II). Similarly, administration of 120 picomoles of CRRETAWAC (SEQ ID NO: 1)/2 ml blood volume, and administration of 15 picomoles of SJ749/2 ml blood volume inhibited angiogenesis by 50%. Based on these results, the skilled artisan can estimate the amounts of such agents required to effectively inhibit angiogenesis in a tissue in an individual such as a human, and routine clinical trials can be used to determine optimal dosages. Assuming, for example, that a human has a blood volume of about six liters, the artisan would know that a range of amounts less than or around about 15 milligrams of an anti-α5β1 antibody can be used in a clinical trial for determining an amount of the agent to be administered to a human. Estimates of an amount to be administered can be adjusted accordingly, for example, where the agent is to be administered locally.

The total amount of an agent antagonist can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a particular agent required to provide an effective amount to a region or regions of angiogenesis associated with. α5β1 integrin expression in an individual depends on many factors including the age and general health of the subject as well as the route of administration, the number of treatments to be administered, and the nature of the agent, including whether the agent is an antibody, a peptide, or a non-peptide small organic molecule. In view of these factors, the skilled artisan would adjust the particular dose so as to obtain an effective amount for efficaciously interfering with the specific binding of α5β1 integrin with its ligand, thereby allowing either for detection of the agent at a region of angiogenesis associated with α5β1 integrin expression for diagnostic purposes, or for reducing or inhibiting such angiogenesis for therapeutic purposes.

An agent useful for detecting or reducing or inhibiting angiogenesis associated with α5β1 integrin expression, or a pharmaceutical composition thereof containing the agent, can be used for treating any pathological condition that is characterized, at least in part, by such angiogenesis. One skilled in the art would know that the agent can be administered by various routes including, for example, orally, or parenterally, including intravenously, intramuscularly, subcutaneously, intraorbitally, intracapsularly, intrasynovially, intraperitoneally, intracisternally or by passive or facilitated absorption through the skin using, for example, a skin patch or transdermal iontophoresis. Furthermore, the agent can be administered by injection, intubation, via a suppository, orally or topically, the latter of which can be passive, for example, by direct application of an ointment or powder containing the agent, or active, for example, using a nasal spray or inhalant. The agent can also be administered as a topical spray, if desire, in which case one component of the composition is an appropriate propellant. The pharmaceutical composition also can be incorporated, if desired, into liposomes, microspheres or other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

As disclosed herein, agents that interfere with α5β1 integrin binding to its ligand can reduce or inhibit angiogenesis associated with α5β1 expression. In addition to the exemplified agent antagonists, other such agents can be identified by detecting agents that interfere α5β1 integrin binding to its ligand. Thus, the invention provides screening assays, which are useful for identifying an agent that reduces or inhibits angiogenesis associated with α5β1 integrin expression in a tissue.

A screening assay of the invention can be performed by contacting a tissue exhibiting angiogenesis associated with α5β1 integrin expression with an agent, and detecting a reduction or inhibition of angiogenesis in the tissue, thereby identifying an agent that reduces or inhibits angiogenesis associated with α5β1 integrin expression in a tissue. A tissue can be contacted with the agent in vivo or ex vivo (see, for example, U.S. Pat. No. 5,622,699). Where a screening method of the invention is performed using an in vitro format, the can be adapted to automated procedure, thus allowing high throughput screening assays for examining libraries of molecules to identify potential α5β1 antagonists, which can reduce or inhibit angiogenesis associated with α5β1 expression. The tissue can be any tissue that undergoes angiogenesis associated with α5β1 integrin expression, for example, malignant neoplastic tissue.

Methods for preparing libraries of molecules, which can be screened using a method of the invention to identify α5β1 antagonists, which reduce or inhibit angiogenesis associated with α5β1 expression, including, for example, oligonucleotide libraries (Gold et al., U.S. Pat. No. : 5,270,163); peptide libraries (Koivunen et al., supra, 1993, 1994); peptidomimetic libraries (Blondelle et al., *Trends Anal. Chem.*, 14:83–92 (1995)); oligosaccharide libraries (York et al., *Carb. Res.*, 285:99–128, (1996); Liang et al., *Science*, 274:1520–1522, (1996); and Ding et al., *Adv. Expt. Med. Biol.*, 376:261–269, (1995)); lipoprotein libraries (de Kruif et al., *FEBS Lett.*, 399:232–236, (1996)); glycoprotein or glycolipid libraries (Karaoglu et al., *J. Cell Biol.*, 130:567–577 (1995)); or chemical libraries containing, for example, drugs or other pharmaceutical agents (Gordon et al., *J. Med. Chem.*, 37:1385–1401 (1994); Ecker and Crook, *Bio/Technology*, 13:351–360 (1995)), including, for example, heterocycles having the general structure (S)-2-phenylsulfonylamino-3-{{{8-(2-pyridinyl aminomethyl)-}-1-oxa-2-azaspiro-{4,5}-dec-2-en-yl}carbonylamino}propionic acid (U.S. Pat. No. 5,760,029). Libraries of diverse molecules also can be obtained from commercial sources.

The following examples are intended to illustrate but not limit the present invention.

EXAMPLE I

α5β1 Integrin is Expressed During Angiogenesis

This Example provides immunohistochemical evidence that α5β1 is expressed in association with newly formed blood vessels in various human and mouse tumors.

Five μm frozen sections of human normal breast and colon, colon carcinoma, breast carcinoma, human tumor xenotransplants in six week old CB17 female SCID mice (Charles River; Wilmington Mass.), and in breast tumors from Mtag mice were fixed for 1 min in acetone, air dried and rehydrated for 5 min in phosphate buffered saline (PBS). Sections were blocked for 2 hr in 8% normal goat serum in PBS and incubated with: 1) 5 μg/ml anti-α5β1 cytoplasmic tail polyclonal antibody (AB1928P; Pharmingen, Inc.; San Diego Calif.) and 5 μg/ml murine anti-human CD31 monoclonal antibody (PECAM; MA-3100; Endogen); 2) 5 μg/ml anti-α5β1 monoclonal antibody and 5 μg/ml rabbit anti-von Willebrand's factor antibody (016P; Biogenex; San Ramon Calif.); or 3) 5 μg/ml anti-fibronectin cell binding peptide monoclonal antibody (784A2A6; Chemicon, Inc.; Temecula Calif.) and 5 μg/ml anti-von Willebrand's factor antibody (016P), in 2% bovine serum albumin (BSA) in PBS for 2 hr at room temperature (RT).

Sections were washed by dipping in six fresh changes of PBS and incubated in 1:400–1:600 dilutions of goat anti-rabbit-FITC and in 1:400–1:600 goat anti-mouse-rhodamine for 1 hr at RT (cross-absorbed secondary antibodies; Biosource International; Camarillo Calif.). Slides were washed, and coverslips were mounted in one drop of Fluoromount-G (Southern Biotechnology Associates; Birmingham Ala.) prior to digital image analysis under fluorescent illumination using a supercooled CCD camera.

Analysis of frozen sections of human colon carcinoma and breast carcinoma for expression of the endothelial cell marker CD31 (PECAM) and integrin α5β1 by two color immunohistochemistry indicated that CD31 positive tumor vessels (stained red) also were positive for integrin α5β1 expression (stained green); vessels positive for both molecules appeared yellow by photomicrography. Large vessels with lumens, as well as large and small vessels without apparent lumens stained positively for integrin α5β1 and CD31. Sections of ovarian and pancreatic carcinoma showed similar patterns of integrin α5β1 expression on blood vessels. In contrast, CD31 positive blood vessels present in sections of normal human colon and breast were negative for integrin α5β1, as were blood vessels in other normal adult tissues, including skin. These results demonstrate that integrin α5β1 expression is upregulated on tumor vasculature and that the majority of blood vessels in these tumor sections are positive for α5β1 expression. The results further demonstrate that α5β1 is not significantly expressed on blood vessels in normal adult tissues.

Tumor tissues also were stained with antibodies directed against fibronectin (stained red) and von Willebrand's Factor (stained green), which is another blood vessel marker. Examination of frozen sections of breast carcinoma and colon carcinoma, as well as normal human breast and colon indicated that the extracellular matrix surrounding tumor vessels was positive for fibronectin expression. In contrast, blood vessels in normal tissues expressed little, if any, fibronectin. Sections of ovarian and pancreatic carcinoma showed similar patterns of fibronectin expression on blood vessels.

Notably, the expression of integrin α5β1 and its ligand, fibronectin, were coordinately upregulated on many of the same blood vessels within human tumor sections. These coordinate expression of these molecules in human tumor tissues is indicative of a possible functional interaction between these proteins. Expression of integrin α5β1 and fibronectin also were observed on tumor vasculature in animal models of neoplasia, including human M21L melanoma tumor xenotransplants in SCID mice and spontaneous mammary tumors in the PyV mouse (see Guy et al., *Mol. Cell Biol.* 12:954–961 (1992), which is incorporated herein by reference, regarding PyV mouse model). Thus, significantly elevated expression of integrin α5β1 and fibronectin is associated with the vasculature in spontaneous tumors and in experimentally induced human and murine tumors compared to normal tissues.

EXAMPLE II

α5β1 And Fibronectin are Required for Angiogenesis

This example demonstrates that fibronectin and the fibronectin receptor integrin α5β1 are involved in angiogenesis in tumors and in growth factor stimulated angiogenesis.

A. METHODS

1. Cell Adhesion Assay

HT29 integrin α5β1$^+$ cells, integrin α5β1$^-$ colon carcinoma cells (Varner et al., *Mol. Biol. Cell* 6:725–740 (1995)), and chick embryo fibroblasts (CEF's) were maintained in DMEM high glucose supplemented with 10% fetal bovine serum (FBS) and gentamycin. Human umbilical vein endothelial cells (HUVEC's) were maintained in M199 medium containing sodium bicarbonate, HEPES, heparin, endothelial cell growth supplement, 20% FBS and gentamycin. Culture media and reagents were from Irvine Scientific (Irvine, Calif.).

The wells of 48 well culture dishes (Costar, Inc.) were coated with 1 µg/ml vitronectin, 2 µg/ml fibronectin (chick embryo fibroblasts and HUVEC's) or 10 µg/ml fibronectin (HT29-α5$^+$ cells) for 1 hr at 37° C., then blocked with 2% heat denatured BSA in PBS for 1 hr. Fifty thousand cells in 250 µl of adhesion buffer were added to triplicate wells containing 250 µl of a solution of 50 µg/ml of an anti-α5β1 function blocking antibody (NKI-SAM-1, JBS5 or IIA1), 50 µg/ml of an anti-α5β1 non-function blocking antibody (HA5 or VC5; Pharmingen, Inc.; San Diego Calif.), 10 µM cyclic peptides (Koivunen et al., *J. Biol. Chem.* 268:20205–20210 (1993); Koivunen et al., *J. Cell Biol.* 124:373380 (1994)), 0–10 µM SJ749 ((S)-2-{(2,4,6-trimethylphenyl)sulfonyl}amino-3-{7-benzyloxycarbonyl-8-(2-pyridinylaminomethyl)-1-oxa-2,7-diazaspiro-{4,4}-non-2-en-3-yl}carbonylamino}propionic acid)), 50 µg/ml of LM609, an anti-αVβ3 function blocking antibody, 50 µg/ml P4C10, an anti-β1 function blocking antibody, 50 µg/ml of an anti-fibronectin cell binding domain monoclonal antibody or 50 µg/ml of an anti-fibronectin N-terminus monoclonal antibody in adhesion buffer (HEPES buffered Hanks balanced salt solution, HBSS, containing 1% BSA, 2 mM MgCl$_2$, 2 mM CaCl$_2$ and 0.2 mM MnCl$_2$).

Cells were allowed to adhere to dishes for 20 min at 37° C. Nonadherent cells were removed by washing each well four times with 500 µl of warm adhesion buffer. Adherent cells were then fixed for 15 min with 3.7% paraformaldehyde in PBS and stained with a 2% crystal violet solution. After extensive water washing to remove excess crystal violet, plates were dried overnight. Crystal violet was extracted by incubation for 15 min in 10% acetic acid and absorbance at 562 nm determined as an indicator of number of cells bound. Each experiment was performed in triplicate, with triplicate samples per condition. Data was presented as percent of adhesion exhibited by the positive control (adhesion medium alone) +/- standard error of measurement.

2. Cell Migration Assays

The lower side of 8 µm pore transwell inserts (Costar, Inc.) were coated with 2 µg/ml of fibronectin, collagen (Collaborative Biomedical Products; Bedford Mass.) or no protein for 1 hr and were blocked with 2% BSA in PBS for 1 hr. The inserts then were placed into 24 well culture dishes containing 500 µl migration buffer in the lower chamber. Twenty-five thousand HUVEC's in 50 µl of migration buffer (HEPES buffered M199 medium containing 1% BSA, 2 MM MgCl$_2$, 2 mM CaCl$_2$ and 0.2 mM MnCl$_2$) were added to the upper chamber of duplicate inserts containing 50 µl of a solution of 50 µg/ml of anti-α5β1 function blocking antibody (NKI-SAM-1, JBS5 or IIA1), 50 µg/ml of anti-α5β1 non-function blocking antibody (HA5 or VC5), or 50 µg/ml of LM609 (an anti-αVβ3 function blocking antibody) in migration buffer, or migration buffer alone.

Cells were allowed to migrate from the upper to the lower chamber for 4 hr at 37° C. Nonmigratory cells were removed from the upper surface by wiping the upper side with an absorbant tip, and cells that had migrated to the lower side of the transwell insert were fixed for 15 min with 3.7% paraformaldehyde in PBS, then stained with a 2% crystal violet solution. After extensive water washing to remove excess crystal violet, the number of cells that had migrated were counted in three representative high power (200X) fields per insert. Data was presented as number of cells migrating +/- standard error of measurement.

3. In Ovo Chick Chorioallantoic Membrane (CAM) Angiogenesis Assay

Ten day old embryonated chicken eggs (McIntyre Poultry; Ramona Calif.) were candled to illuminate blood vessels under the shell and an area with a minimum of small blood vessels is identified. The CAM was dropped away from the eggshell in this area by grinding a small hole in the mineralized shell and applying pressure to the underlying inner shell membrane. This procedure caused an air pocket to shift from the wide end of the egg to the identified area and forcing a circular region of the CAM approximately 2 cm in diameter to drop away from the shell. A window was cut in the egg shell and a cortisone acetate pre-treated filter disc 5 mm in diameter that had been saturated in 1 µg/ml bFGF, VEGF, TNFα, IL-8 (Genzyme, Inc.; Cambridge Mass.) or saline was placed on the CAM. The window in the shell was sealed with adhesive tape and the egg was incubated for four days.

A range of 0–25 μg in 25 μl of function blocking anti-α5β1 or a control non-function blocking anti-α5β1, 0–25 μM in 25 μl cyclic peptide (CRRETAWAC; SEQ ID NO: 1) or scrambled control peptide (CATAERWRC; SEQ ID NO: 2; Koivunen et al., *J. Biol. Chem.* 268:20205–20210 (1993); Koivunen et al., *J. Cell Biol.* 124:373380 (1994)), 0–25 μM in 25 μl of SJ749, an inactive control small molecule or 25 μl of saline were applied to the growth factor saturated filter 24 hours later. Anti-fibronectin antibodies (25 μg in 25 μl) also were applied topically to the CAM.

Fibronectin, vitronectin and fibronectin fragments (59 pmol in a final volume of 25 μl) were applied to stimulated or unstimulated CAM's. Peptide or small molecule antagonists of α5β1 (at a final serum concentration of 0–25 μM) also were injected intravenously into the chick circulation 24 hr later. CAM's were harvested on the fourth day of stimulation. Blood vessel branch points in the 5 mm filter disk area were counted at 30× magnification in a blinded fashion as a size-independent quantitative indicator of vascular sprouting in response to growth factors. Angiogenesis is characterized by the sprouting of new vessels in response to growth factors. Thus, counting of blood vessel branch points is a useful quantitative means of obtaining an angiogenic index (Brooks et al., In "Methods in Molecular Biology" (Humana Press 1999). At least ten embryos were used per treatment group. Each experiment was performed a minimum of three times.

Data was evaluated in terms of average number of blood vessel branch points per treatment group +/− standard error of measurement. Statistical analyses were performed using Student's t-test. Representative CAMS from each treatment group were photographed at 10× magnification. In some cases, CAM tissue excised from the egg was frozen in OCT (Baxter; McGraw Park Ill.) in liquid nitrogen, cut into 5 μm sections, air dried and processed for immunohistochemical analysis as described in Example I, except without fixation.

4. Integrin Receptor Ligand Binding Assays

Integrin αVβ3 and α5β1 receptor purified from human placenta were obtained from Chemicon International. Platelet integrin αIIbβ3 was purified from platelets according to established procedures. Receptors were coated (100 μl/well) on Costar (3590) high capacity binding plates overnight at 4° C. Coating solution was discarded and plates were washed once with blocking/ binding (B/B) buffer (50 mM Tris HCl, pH 7.4, 100 mM NaCl, 2 mM CaCl$_2$, 1 mM MgCl$_2$, 1 mM MnCl$_2$ and 1% BSA).

One hundred ten microliters of B/B buffer was applied for 60 min at RT. Thirty μl of biotinylated extracellular matrix protein ligand (fibronectin for integrin α5β1, vitronectin for integrin αVβ3 and fibrinogen for integrin αIIbβ3) plus 50 μl of either SJ749 in B/B buffer or B/B buffer alone were added to each well, and incubated for 25 min at RT. Plates were washed twice with B/B buffer and incubated 1 hr at RT, with anti-biotin alkaline phosphatase (100 μl/well) in B/B buffer. Finally, plates were washed twice with B/B followed by the addition of 100 μl of phosphatase substrate (1.5 mg/ml). Reaction was stopped by adding 2N NaOH (25 μl/well), and the developed color was read at 405 nm.

B. RESULTS

1. Antibody specific for the cell binding domain of fibronectin inhibits attachment and migration of cells expressing α5β1 integrin to fibronectin in vitro and inhibits angiogenesis in vivo in CAM's Since fibronectin was localized to 5β1-expressing blood vessels in tumors and growth factor treated tissues, the effects of fibronectin and of function blocking anti-fibronectin antibodies on angiogenesis was evaluated.

An in vitro cell adhesion assay was used to determine, first, whether an antibody directed against the central cell binding domain peptide (anti-CBP antibody) or an antibody against an N-terminal peptide of fibronectin (anti-NT antibody) of human and chicken fibronectin inhibited cell adhesion to fibronectin. The anti-CBP antibody significantly inhibited the adhesion to fibronectin of integrin α5β1 positive cells, including α5β1$^+$ HT29 colon carcinoma cells, CEF's, and HUVEC's. HUVEC adhesion was blocked 70+/−3% by the anti-CBP antibody. In contrast, the anti-NT antibody was ineffective in blocking cell adhesion to fibronectin. These results demonstrate that the CBP domain of fibronectin is required for adhesion of cells expressing α5β1 integrin.

Function-blocking monoclonal antibody antagonists of integrin α5β1, but not control (non-function blocking) anti-α5β1 integrin monoclonal antibodies, selectively inhibited HT29 α5$^+$ (100+/−6%), CEF (89.7+/−3.4%), and HUVEC (72+/−2.5%) adhesion to fibronectin, but did not inhibit attachment to vitronectin; however, LM609, an anti-αVβ3 specific antibody inhibited attachment of the cells to vitronectin. These results demonstrate that α5β1 binding to fibronectin is required for adhesion α5β1 expressing cells to fibronectin.

As angiogenesis depends in part on endothelial cell migration and invasion, the ability of anti-α5β1 antibodies to block HUVEC migration also was evaluated. Migration of HUVEC's on fibronectin was significantly inhibited (87+/−2%) by function blocking antibodies directed against integrin α5β1, whereas this antibody did not affect endothelial cell migration on other matrix proteins, including collagen. These results demonstrate that α5β1 integrin also is involved in fibronectin mediated cell migration.

The roles of fibronectin and of α5β1 on angiogenesis was examined in vivo was examined using the CAM assay. To assess the role of fibronectin in angiogenesis in vivo, CAM's from ten day old embryos were stimulated with bFGF or VEGF. Twenty-four hr later, anti-fibronectin antibodies were directly applied to the CAM's, then, two days later, CAM's were excised and blood vessels were quantified by counting vessel branch points.

The anti-CBP antibody inhibited the growth of new blood vessels induced by bFGF by 75+/−10% (p=0.002), whereas the anti-NT antibody had a only minimal effect (34+/−15% inhibition, p=0.02). The anti-CBP antibody also inhibited VEGF angiogenesis by 71+/−7% (p=0.02), as did the anti-NT antibody (89+/−17% inhibition, p=0.035). In contrast to anti-fibronectin antibodies, function blocking antibodies directed against vitronectin had no significant effect on angiogenesis. These results indicate that the cell-binding domain of fibronectin plays a critical role in angiogenesis, and that the N-terminal domain of fibronectin also may contribute to some angiogenesis.

To further demonstrate a specific functional association between fibronectin and angiogenesis stimulation, fibronectin and vitronectin were directly applied to the CAM's of ten day old embryos in the presence or absence of growth factors. In the absence of growth factor addition, neither fibronectin nor vitronectin promoted angiogenesis. Equimolar amounts of intact human fibronectin, a 120 kD fragment of fibronectin with the RGD containing cell binding domain or a 40 kD C-terminal chymotryptic fibronectin fragment which lacks the RGD containing cell-binding domain (Chemicon; Temecula Calif.) were applied to bFGF stimulated CAM's and angiogenesis was examined.

Intact fibronectin enhanced growth factor stimulated angiogenesis at least 46+/−11% (p=0.04). The 120 kD cell binding fragment of fibronectin also significantly enhanced angiogenesis (65+/−20%; p=0.05); in contrast, the 40 kD fragment of fibronectin had no significant effect. Furthermore, anti-α5β1 integrin antibodies reversed this process, demonstrating that fibronectin-enhanced angiogenesis was dependent on integrin α5β1 activity (see below). Application of vitronectin to bFGF stimulated CAM's had no effect on vessel number. Addition of fibronectin or vitronectin to VEGF stimulated CAM's also did not potentiate the angiogenic effect of VEGF. These results demonstrate that fibronectin and the endothelial cell integrin α5β1 have functional roles in growth factor-induced angiogenesis.

The ability of anti-α5β1 antibodies to impact growth factor-induced angiogenesis on the chick CAM also was examined. Twenty-four hr after stimulating angiogenesis with bFGF, anti-α5β1 antibodies were directly applied to the growth factor saturated filter disk or were injected intravenously into the embryonic circulation. The antibody antagonists of integrin α5β1 blocked bFGF-induced angiogenesis on the CAM by at least 88+/−6% (p=0.01), whereas control non-function blocking anti-α5β1 antibodies had no significant effect. Applications of function-blocking or control anti-α5β1 antibodies to unstimulated CAM's had no effect on the number or integrity of blood vessels present within the application area. Similarly, anti-αVβ3 antibody also blocked angiogenesis induced by bFGF by 65+/−10% (p=0.008).

Distinct growth factors can induce selective pathways of angiogenesis that activate or utilize distinct integrins. For example, integrin αVβ3 participates in the bFGF and TNFα pathways of angiogenesis, while αVβ5 participates in the VEGF and TGFα pathways. Accordingly, the role of other integrins in growth factor induced angiogenesis was examined further.

When angiogenesis was stimulated with TNFα or IL-8, anti-α5β1 antibodies blocked angiogenesis by an average of 70.4+/−12% (p=0.04) and 85+/−4.8% (p<0.0001), respectively, and, in some experiments anti-α5β1 antibodies inhibited TNFα and IL-8 angiogenesis by up to 99+/−5% (p=0.005). Similarly, antibody antagonists of integrin αVβ3 blocked TNFα and IL-8 angiogenesis by 93.6+/−6.2% (p=0.004) and 77+/−5.2% (p=0.0001), respectively. However, when angiogenesis was induced with VEGF, antibody antagonists of integrin α5β1 failed to block angiogenesis, whereas anti-αVβ5 antibody blocked VEGF-induced angiogenesis by 99+/−0.1% (p=0.004). When anti-α5β1 integrin and anti-αVβ3 integrin antibodies were applied in combination to bFGF stimulated CAM's, no additive or synergistic inhibitory effects were observed, suggesting that these integrins participate in the same angiogenic pathway.

These results demonstrate that an interaction of α5β1 integrin with the cell-binding domain of fibronectin is involved in growth factor-induced angiogenesis in vivo, and that an anti-α5β1 antibody can interfere with such angiogenesis. The results also indicate that integrin α5β1 regulates the same pathway of angiogenesis as does αVβ3 and that this pathway is distinct from that regulated by αVβ5.

2. Peptide and nonpeptide small organic molecule α5β1 antagonists inhibit attachment and migration of cells expressing α5β1 integrin to fibronectin in vitro and inhibit angiogenesis in vivo in CAM's.

The ability of peptide and nonpeptide small organic molecule antagonists of α5β1 integrin to interfere with cell interactions with fibronectin and with growth factor induced angiogenesis also was examined.

Non-antibody antagonists of integrin α5β1 potently inhibited cell attachment to fibronectin. The selective cyclic peptide antagonist of integrin α5β1, CRRETAWAC (SEQ ID NO: 1), significantly inhibited adhesion of α5+ HT29 colon carcinoma cells, CEF's and HUVEC's to fibronectin, but not to vitronectin, whereas a "scrambled" control peptide (CATAERWRC; SEQ ID NO: 2) had little effect on cell adhesion to either fibronectin or vitronectin. CRRETAWAC (SEQ ID NO: 1), but not the control peptide, also interfered with endothelial cell migration on fibronectin, but not on other matrix proteins such as collagen. The cyclic peptide antagonist of α5β1 also significantly blocked bFGF-induced angiogenesis (90+/−6%; p<0.0001), whereas control peptides did not inhibit angiogenesis. The peptide antagonists of integrin α5β1 failed to block VEGF angiogenesis.

The α5β1 selective nonpeptide small organic molecule antagonist, SJ749, blocked the adhesion of these cells to fibronectin in a concentration-dependent manner (half maximal inhibitory concentration of 0.8 μM for α5+ HT29 cells; FIG. 1), but was ineffective in blocking cell attachment to vitronectin or other extracellular matrix ligands. SJ749 also selectively inhibited ligand binding to α5β1 and was substantially less effective in blocking ligand binding to αVβ3 and other integrins.

The nonpeptide small organic molecule antagonist of integrin α5β1 also was highly effective in blocking endothelial cell migration on fibronectin, but not on other matrix proteins such as collagen. SJ749 also blocked bFGF-induced angiogenesis on chick CAM's in a dose-dependent manner when applied either topically or systemically (FIG. 2), whereas control nonpeptide molecules did not inhibit angiogenesis, even at the highest dose tested. Like the other α5β1 antagonists, SJ749 did not block VEGF angiogenesis.

These results demonstrate that peptide and nonpeptide small organic molecule antagonists of α5β1 significantly and selectively interfere with the function of human and chick α5β1, similarly to anti-α5β1 antibodies. More specifically, systemic administration of antibody, peptide and nonpeptide small molecule antagonists inhibited growth factor-induced angiogenesis with $IC_{50}$'s of approximately 5 μg, 120 pmoles and 15 pmoles, respectively, per 2 ml blood volume of the chick embryos. These results also confirm that the fibronectin receptor integrin α5β1 contributes to growth factor angiogenesis on the CAM.

EXAMPLE III

α5β1 Antagonists Inhibit Growth Factor Induced Angiogenesis in Human Skin in SCID Mice This example demonstrates that α5β1 antagonists inhibit angiogenesis in human skin grown in SCID mice.

Engraftment of SCID mice with human skins was performed as previously described (Brooks et al., *J. Clin. Invest.* 96:1815–1822 (1995)). SCID mice were engrafted with an 8 mm×13 mm piece of human neonatal foreskin. Fresh human neonatal foreskins were obtained from the Cooperative Human Tissue Network of the National Institutes of Health and were stored in RPMI-1640 medium supplemented with 2% fetal bovine serum and 1% gentamicin.

Four weeks after engraftment, after the skin had completely healed, 50 μl of growth factor depleted matrigel (Becton Dickenson; Bedford Mass.) reconstituted with 1 μg/ml basic fibroblast growth factor (bFGF), with 1 μg/ml bFGF containing 25 μg/ml anti-α5β1 function blocking monoclonal antibody or with 1 μg/ml bFGF containing 25 μg/ml non-function blocking anti-α5β1 monoclonal antibody was injected intradermally in the center of each engrafted skin. Three days later, the human skin was excised from the mouse. Boundaries were easily observed since the human skin was pink and hairless; the mouse skin was covered with white fur. The human skin was embedded in freezing medium, frozen and sectioned. Sections were stained for the presence of human blood vessels with anti-CD31, as described in Immunohistochemical analyses of blood vessel densities. Data was presented as mean CD31 positive blood vessel numbers per 100x microscopic field, +/− standard error of measurement. Statistical analyses were performed using Student's t-test.

Human neonatal foreskin engrafted onto SCID mice was injected intradermally with growth factor depleted basement membrane impregnated with bFGF in the presence or absence of the function-blocking and control anti-α5β1 antibodies. Analysis of the human skin after three days for the presence of human CD31 positive blood vessels. The addition of function-blocking α5β1 antibody selectively blocked angiogenesis induced by the growth factor, and reduced the number of CD31 positive blood vessels per high power field by 94+/−4.7% (P=0.006).

These results demonstrate that integrin α5β1 has a functional role in the angiogenic response to growth factors of human blood vessels, and that an antagonist of α5β1 binding can reduce or inhibit growth factor stimulated angiogenesis in human skin.

EXAMPLE IV

α5β1 Antagonists Inhibit Tumor Growth

This example demonstrates that α5β1 antagonists inhibit angiogenesis in human tumors in a CAM model system.

The chick CAM tumor assay was performed by placing ten million tumor cells on the surface of a CAM, and culturing the cells for one week. The resulting tumors were excised and cut into 50 mg fragments. These fragments were placed on additional CAM's and treated topically the following day with 25 µg in 25 µl of anti-α5β1 or a control non-function blocking anti-α5β1, or systemically by intravenous injection with a final serum concentration of 25 µM cyclic peptides or 25 µM SJ7549 and 25 µM scrambled control peptide or 25 µM inactive small molecule or 25 µl of saline (blood volume of chick embryo is approximately 2 ml). Forty-eight hours later, CAM's were excised from the egg and the number of blood vessels entering the tumors were counted (as vessel branch points).

Data was presented as mean blood vessel number per treatment group (+/− standard error of measurement). Each treatment group incorporated at least ten tumors per experiment. Representative tumors were photographed at 10x magnification. Tumors were excised from the egg and tumor weights were determined for each tumor. Data was presented as mean tumor weight per treatment group (+/− standard error of measurement). Statistical analyses were performed using Student's t-test.

HT29 colon carcinoma cells lacking α5β1 expression were grown on the CAM's of 10-day old embryos. These tumor cells secrete several angiogenic growth factors, including VEGF, TGFα, TGFβ, TNFα, and IL-8 (Anzano et al., Cancer Res. 49:2898–2904 (1989); Varner et. al., supra, 1995; Ellis et al., J. Biol. Chem. 273:1052–1057 (1998)). Integrin α5β1 negative tumor cells were used to distinguish the potential anti-tumor effects from anti-vasculature effects of integrin α5β1 antagonists.

Treatment with function-blocking, but not control, antibodies significant reduced (70+/−10%, p=0.02) the number of tumor-associated blood vessels. No significant morphological or quantitative difference was observed between saline and control antibody treated tumors or their associated blood vessels. Furthermore, treatment with function-blocking anti-α5β1 antibodies resulted in tumor regression. Anti-α5β1 treated tumors were 32% smaller than control treated tumors (p=0.02).

Intravenous administration of cyclic peptide inhibitors of integrin α5β1 and nonpeptide small molecule inhibitors of integrin α5β1 also induced tumor regression on the CAM, whereas control peptide or control nonpeptide treated tumors continued to increase in size. Tumors treated with peptide and nonpeptide inhibitors were 31% and 51% smaller than control treated tumors, respectively (p=0.003). Tumor cells remained integrin α5β1 negative throughout the course of the experiment, indicating that the anti-tumor effects were based on the targeting of the tumor associated blood vessels.

The effect of α5β1 antagonists on tumor angiogenesis in α5β1$^+$ Hep 3 squamous carcinoma cells also was examined. Treatment of the tumors with function-blocking anti-α5β1 resulted in tumor regression, with the tumors being 45% smaller than control tumors (p=0.046). No significant morphological or quantitative differences were observed between saline and control antibody treated tumors.

These results demonstrate that targeting vascular cell integrin α5β1 inhibits tumor angiogenesis and tumor growth, and that antagonists of integrin α5β1 are potent inhibitors of tumor growth and tumor-induced angiogenesis.

Although the invention has been described with reference to the examples provided above, it should be understood that various modifications can be made with departing from the spirit of the invention. Accordingly, the invention is limited only by the claims.

What is claimed is:

1. A method of reducing or inhibiting angiogenesis in a tissue, comprising contacting α5β1 integrin in the tissue with an α5β1 antagonist selected from the group consisting of an anti-alpha 5 beta 1 integrin antibody or an alpha 5 beta 1 integrin binding fragment of said antibody, wherein said antagonist induces growth factor stimulated endothelial cell apoptosis and interferes with specific binding of the α5β1 integrin to a ligand expressed in the tissue, thereby reducing or inhibiting angiogenesis in the tissue.

2. A method of reducing or inhibiting angiogenesis in a tissue in an individual, comprising administering to the individual an α5β1 antagonist selected from the group consisting of an anti-alpha 5 beta 1 integrin antibody or an alpha 5 beta 1 integrin binding fragment of said antibody, wherein said antagonist induces growth factor stimulated endothelial cell apoptosis and interferes with the specific binding of α5β1 integrin to a ligand expressed in the tissue, thereby reducing or inhibiting angiogenesis in the tissue in the individual.

3. A method of reducing or inhibiting angiogenesis in an individual having a pathological condition associated with angiogenesis comprising administering to the individual an α5β1 antagonist selected from the group consisting of an anti-alpha 5 beta 1 integrin antibody or an alpha 5 beta 1 binding fragment of said antibody, wherein said antagonist induces growth factor stimulated endothelial cell apoptosis and interferes with specific binding of α5β1 integrin to a ligand in a tissue associated with the pathological condition, thereby reducing or inhibiting angiogenesis in the individual.

4. The method of claim 1, wherein the ligand is fibronectin.

5. The method of claim 1, wherein the tissue comprises ocular tissue.

6. The method of claim 5, wherein the ocular tissue is selected from the group consisting of retina, macula and cornea.

7. The method of claim 1, wherein the tissue comprises a neoplasm.

8. The method of claim 7, wherein the neoplasm is a malignant neoplasm.

9. The method of claim 8, wherein the malignant neoplasm is a metastatic malignant neoplasm.

10. The method of claim 8, wherein the malignant neoplasm is a carcinoma.

11. The method of claim 1, wherein the antagonist is linked to a cytotoxin.

12. The method of claim 11, wherein the cytotoxin is a cancer chemotherapeutic drug.

13. The method of claim 2, wherein the individual is a human.

14. The method of claim 3, wherein the pathological condition is a neoplasm.

15. The method of claim 14, wherein the neoplasm is a malignant neoplasm.

16. The method of claim 15, wherein the malignant neoplasm is a metastatic malignant neoplasm.

17. The method of claim 15, wherein the malignant neoplasm is a carcinoma.

18. The method of claim 17, wherein the carcinoma is selected from the group consisting of a breast carcinoma, a colon carcinoma, an ovarian carcinoma and a pancreatic carcinoma.

19. The method of claim 15, wherein the malignant neoplasm is selected from the group consisting of a sarcoma, a mesothelioma, a teratocarcinoma, an astrocytoma, and a glioblastoma.

20. The method of claim 3, wherein the individual is a human.

21. The method of claim 3, wherein the antagonist is administered intravenously.

22. The method of claim 3, wherein the antagonist is administered orally.

23. The method of claim 14, wherein the antagonist is administered into a neoplasm.

24. The method of claim 3, wherein the pathological condition is associated with the eye.

25. The method of claim 24, wherein the pathological condition is selected from the group consisting of diabetic retinopathy and macular degeneration by neovascularization.

26. The method of claim 24, wherein the antagonist is administered in the form of eye drops.

27. The method of 24, wherein the antagonist is administered intravenously.

28. The method of claim 24, wherein the antagonist is administered orally.

29. The method of claim 3, wherein the antagonist is administered at a dose of 0.0001 to 100 mg/kg body weight.

* * * * *